United States Patent
Tatsutani et al.

(10) Patent No.: US 8,752,440 B2
(45) Date of Patent: Jun. 17, 2014

(54) SAMPLE PROCESSING APPARATUS AND METHOD FOR TRANSPORTING RACK

(75) Inventors: Hiroo Tatsutani, Kobe (JP); Nobuyoshi Yamakawa, Kobe (JP); Nobuhiro Kitagawa, Akashi (JP); Tomoyuki Asahara, Kobe (JP)

(73) Assignee: Sysmex Corporation, Kobe (JP)

( * ) Notice: Subject to any disclaimer, the term of this patent is extended or adjusted under 35 U.S.C. 154(b) by 261 days.

(21) Appl. No.: 13/115,689

(22) Filed: May 25, 2011

(65) Prior Publication Data

US 2011/0290040 A1    Dec. 1, 2011

(30) Foreign Application Priority Data

May 27, 2010 (JP) .................................. 2010-121992

(51) Int. Cl.
*G01N 35/04* (2006.01)
*G01N 35/02* (2006.01)
*G01N 1/22* (2006.01)

(52) U.S. Cl.
USPC ............................. 73/863.01; 422/65; 422/67

(58) Field of Classification Search
USPC .................................... 73/863.01; 422/63–67
See application file for complete search history.

(56) References Cited

U.S. PATENT DOCUMENTS

| | | | | |
|---|---|---|---|---|
| 5,380,488 A | * | 1/1995 | Wakatake | 422/65 |
| 5,972,295 A | * | 10/1999 | Hanawa et al. | 422/65 |
| 6,117,683 A | * | 9/2000 | Kodama et al. | 436/47 |
| 6,261,521 B1 | * | 7/2001 | Mimura et al. | 422/67 |
| 6,599,749 B1 | * | 7/2003 | Kodama et al. | 436/47 |
| 8,252,233 B2 | * | 8/2012 | Tokieda et al. | 422/65 |
| 2005/0036912 A1 | * | 2/2005 | Yamakawa et al. | 422/65 |
| 2005/0036913 A1 | * | 2/2005 | Yamakawa et al. | 422/65 |
| 2005/0196320 A1 | * | 9/2005 | Veiner et al. | 422/63 |
| 2005/0214166 A1 | * | 9/2005 | Itoh | 422/65 |
| 2007/0207056 A1 | * | 9/2007 | Veiner et al. | 422/63 |
| 2008/0310999 A1 | * | 12/2008 | Yagi et al. | 422/65 |
| 2009/0220379 A1 | * | 9/2009 | Wakamiya et al. | 422/65 |
| 2010/0093097 A1 | * | 4/2010 | Kawamura | 436/43 |
| 2010/0212438 A1 | * | 8/2010 | Tanaka et al. | 73/864.81 |
| 2010/0248374 A1 | * | 9/2010 | Kitagawa et al. | 436/47 |
| 2010/0282003 A1 | * | 11/2010 | Hamada et al. | 73/863.91 |
| 2011/0054807 A1 | * | 3/2011 | Mizumoto et al. | 702/35 |
| 2011/0065193 A1 | * | 3/2011 | Kitagawa et al. | 436/43 |
| 2011/0076193 A1 | * | 3/2011 | Kitagawa et al. | 422/65 |
| 2011/0076194 A1 | * | 3/2011 | Kitagawa et al. | 422/65 |
| 2011/0158851 A1 | * | 6/2011 | Kitagawa | 422/67 |

FOREIGN PATENT DOCUMENTS

JP    2009-270869 A    11/2009

* cited by examiner

*Primary Examiner* — Peter MacChiarolo
*Assistant Examiner* — Natalie Huls
(74) *Attorney, Agent, or Firm* — Brinks Gilson & Lione

(57) ABSTRACT

A sample processing apparatus, comprising: a plurality of sample processing units each configured to process a sample; at least one transport device configured to provide a transport path along which a rack is transported to or from one of the plurality of sample processing units, wherein a rack comprises a plurality of positions configured to hold containers thereat, and at least some of the positions are correlated to at least some of the sample processing units; a controller comprising at least one processor and at least one memory that stores computer programs executed by the at least one processor to: direct the at least one transport device to transport the rack to deliver a container held therein to a sample processing unit correlated to a position of the container at which the container is held in the rack.

23 Claims, 19 Drawing Sheets

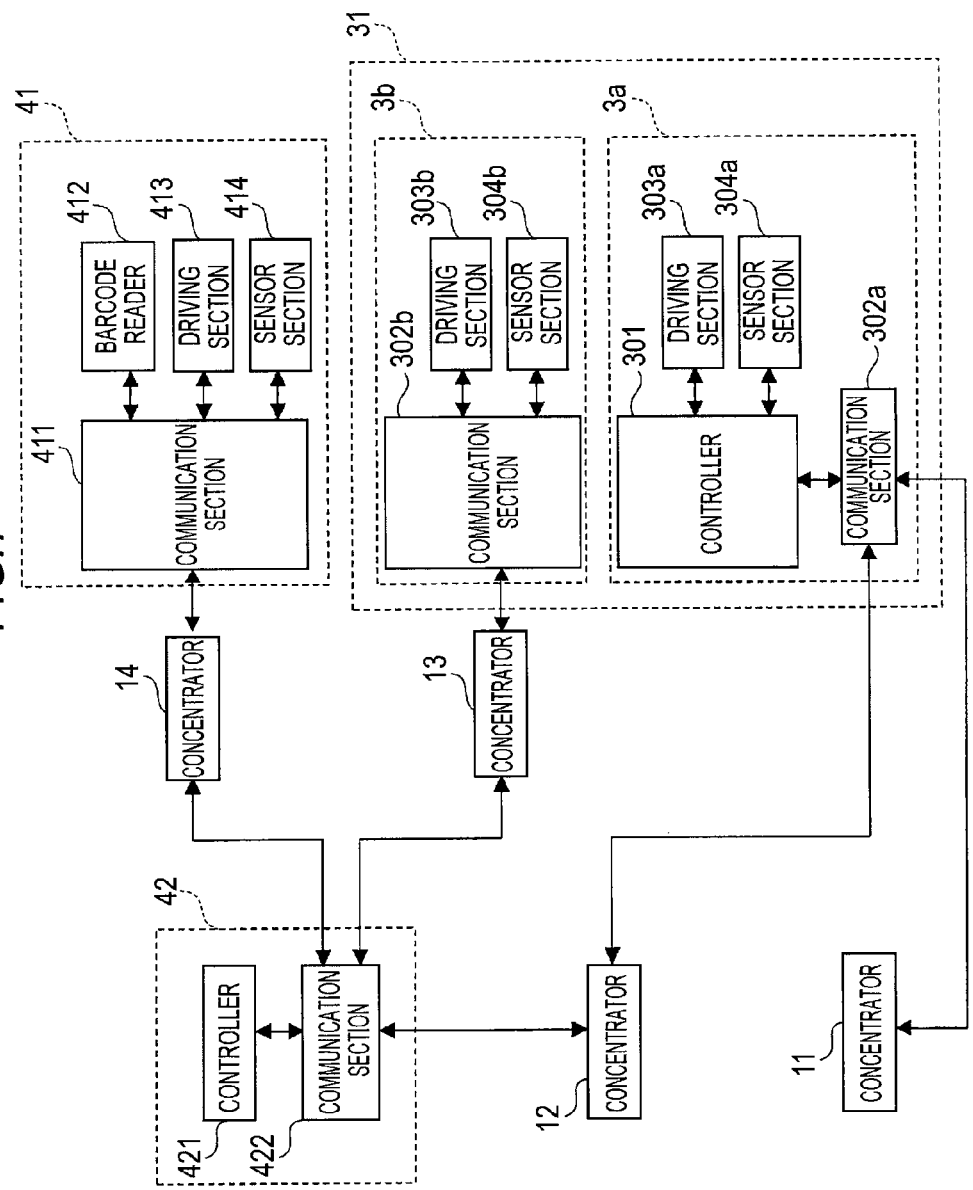

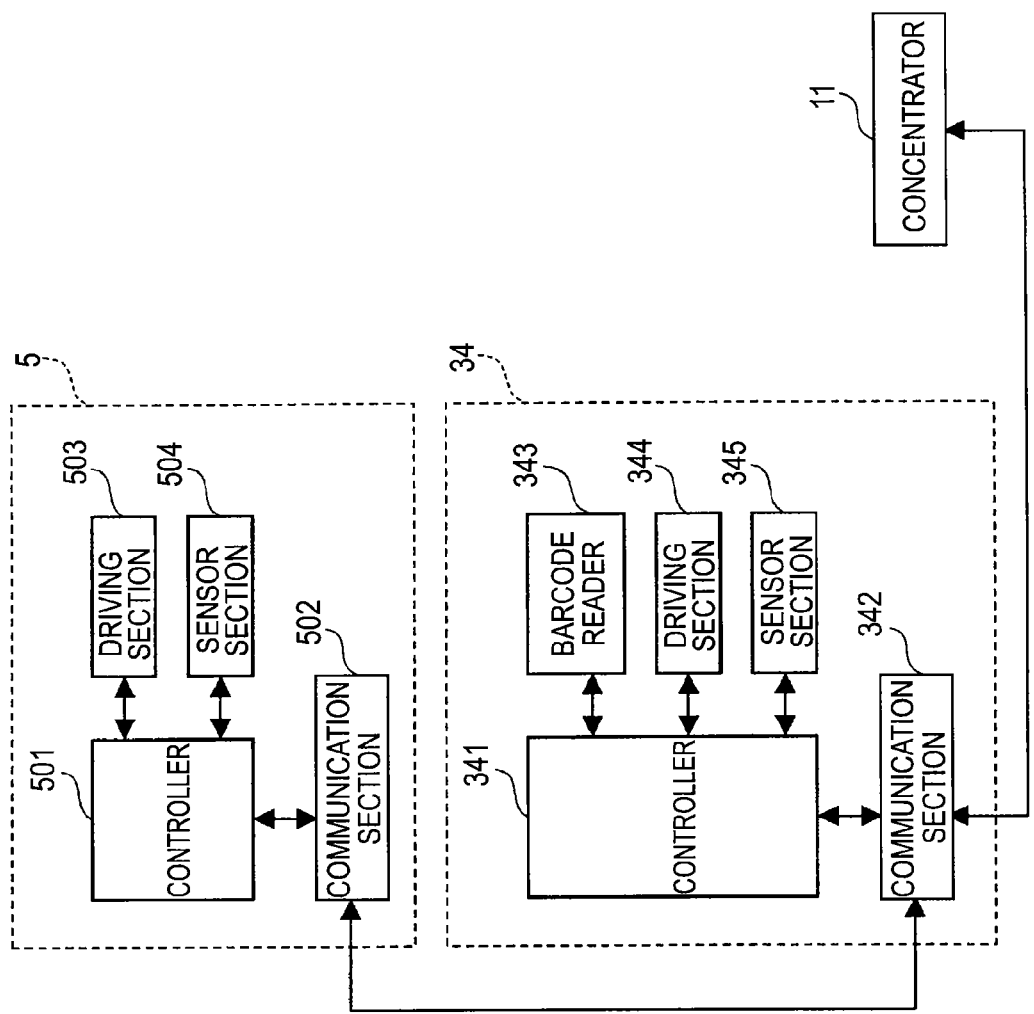

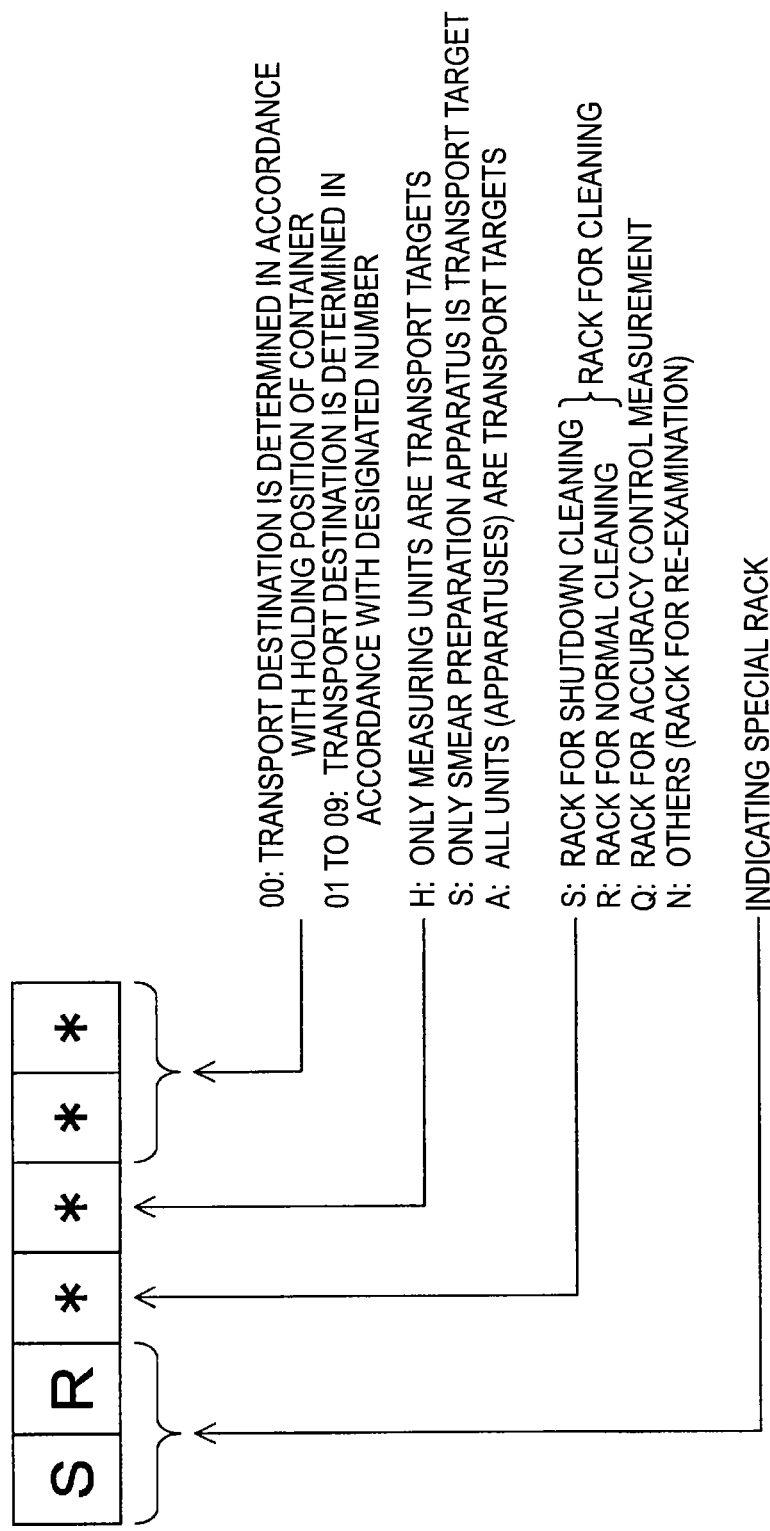

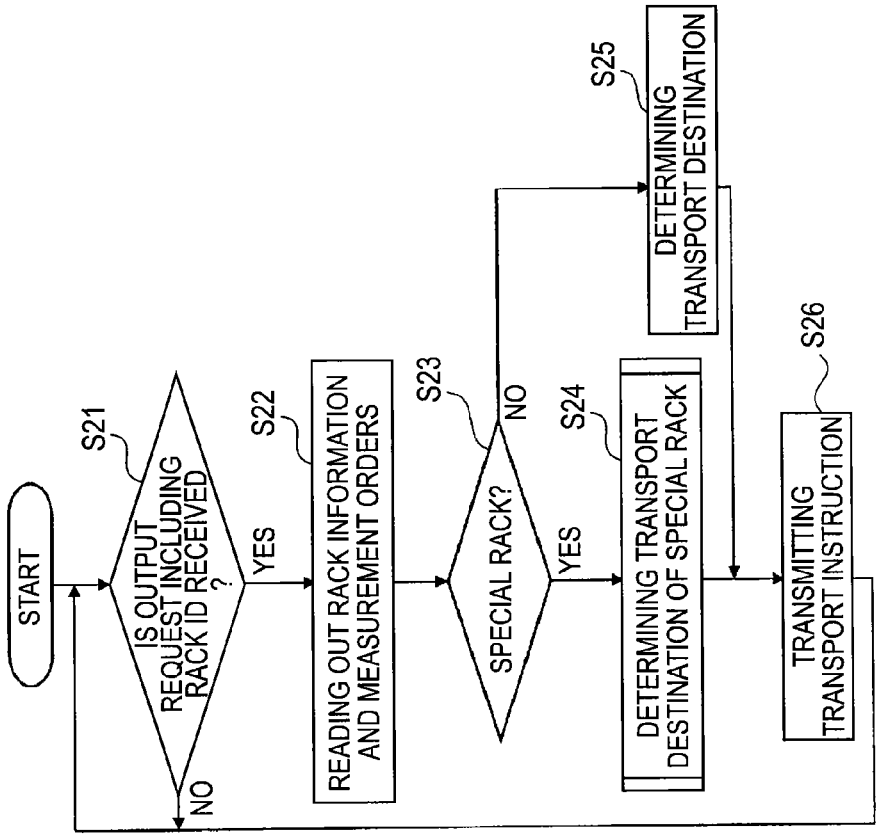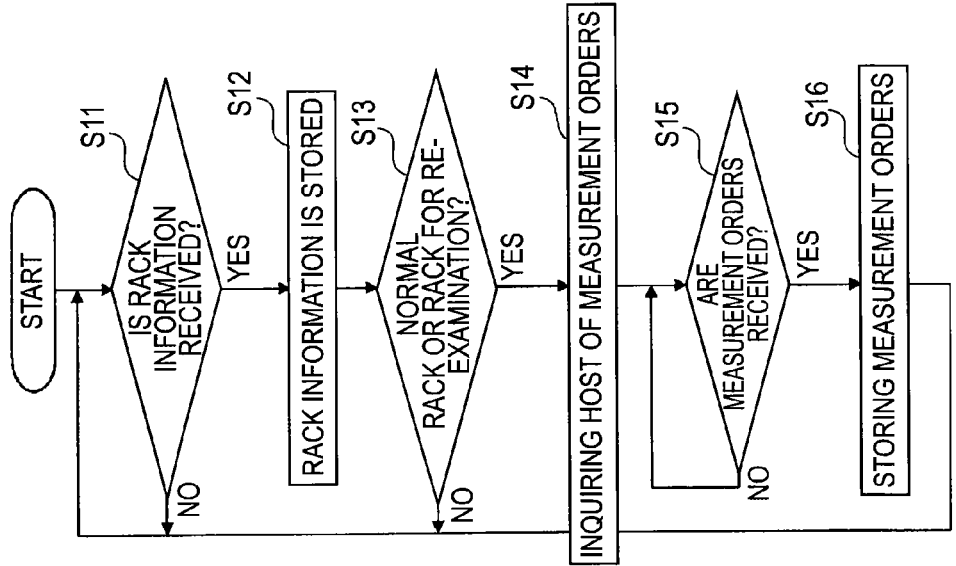

FIG.11

| RACK ID | RACK INFORMATION | | | | |
|---|---|---|---|---|---|
| | HOLDING POSITION | CONTAINER ID | MEASUREMENT ORDER | TRANSPORT DESTINATION | SUCTION NECESSITY |
| SRNA00 | 1 | ..... | ..... | H1 | SUCTION IS NOT NEEDED |
| | 2 | ..... | ..... | H2 | SUCTION IS NEEDED |
| | 3 | — | — | — | SUCTION IS NOT NEEDED |
| | 4 | ..... | ..... | SP1 | SUCTION IS NOT NEEDED |
| | 5 | — | — | — | SUCTION IS NOT NEEDED |
| | 6 | — | — | — | SUCTION IS NOT NEEDED |
| | 7 | — | — | — | SUCTION IS NOT NEEDED |
| | 8 | — | — | — | SUCTION IS NOT NEEDED |
| | 9 | — | — | — | SUCTION IS NOT NEEDED |
| | 10 | — | — | — | SUCTION IS NOT NEEDED |

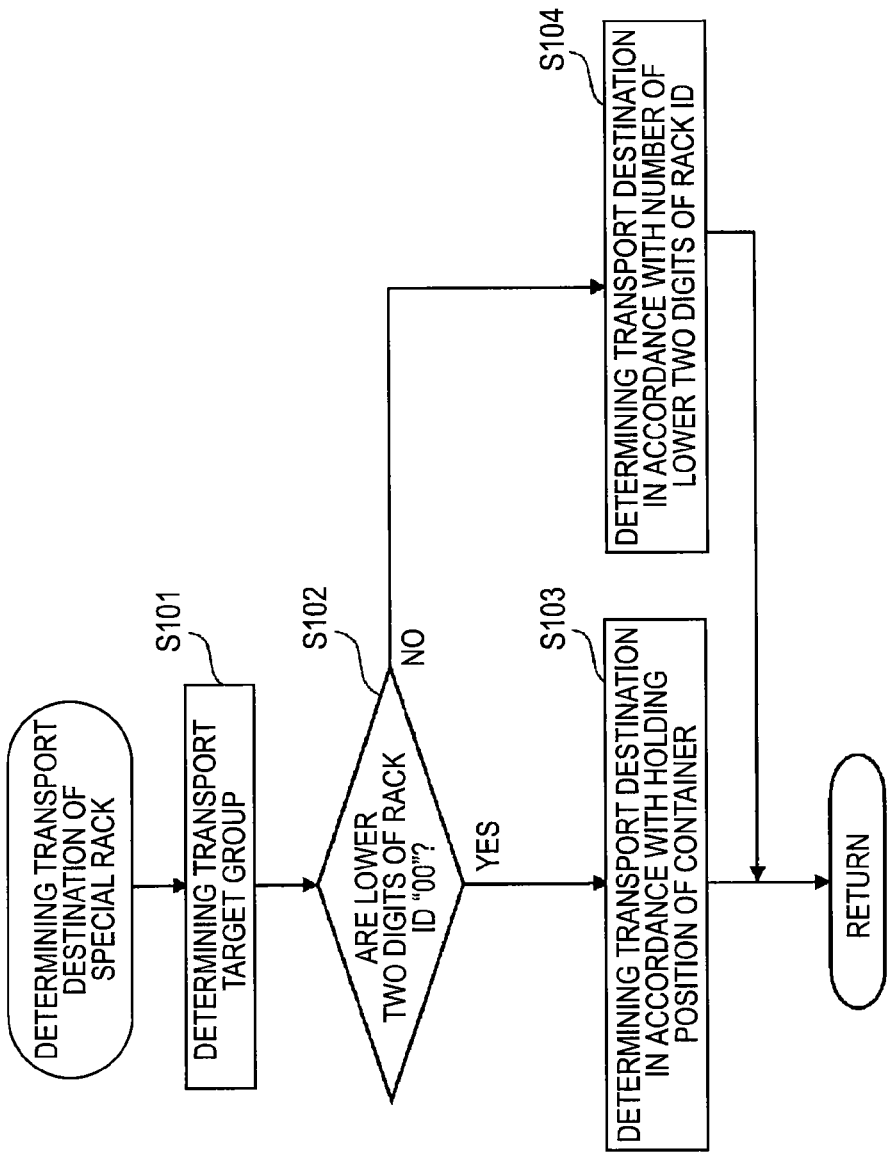

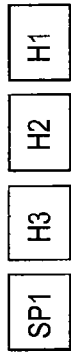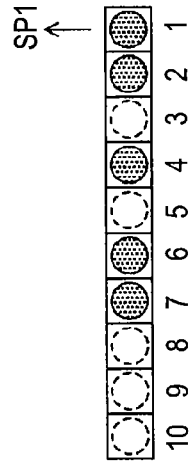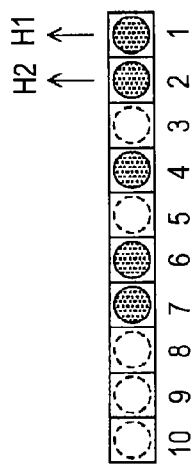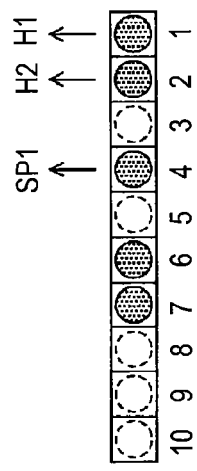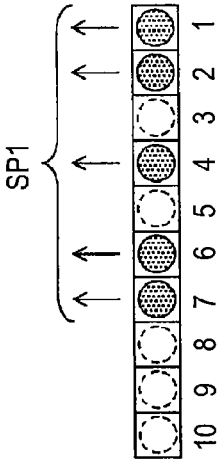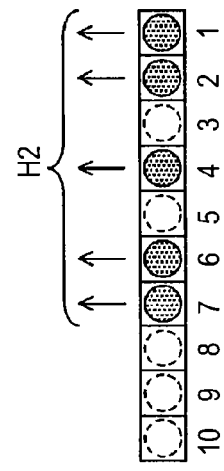
FIG.13A UNIT CONFIGURATION
FIG.13B RACK ID:SRRA00
FIG.13C RACK ID:SRRH00
FIG.13D RACK ID:SRRS00
FIG.13E RACK ID:SRSA02
FIG.13F RACK ID:SRQH03
FIG.13G RACK ID:SRNS01

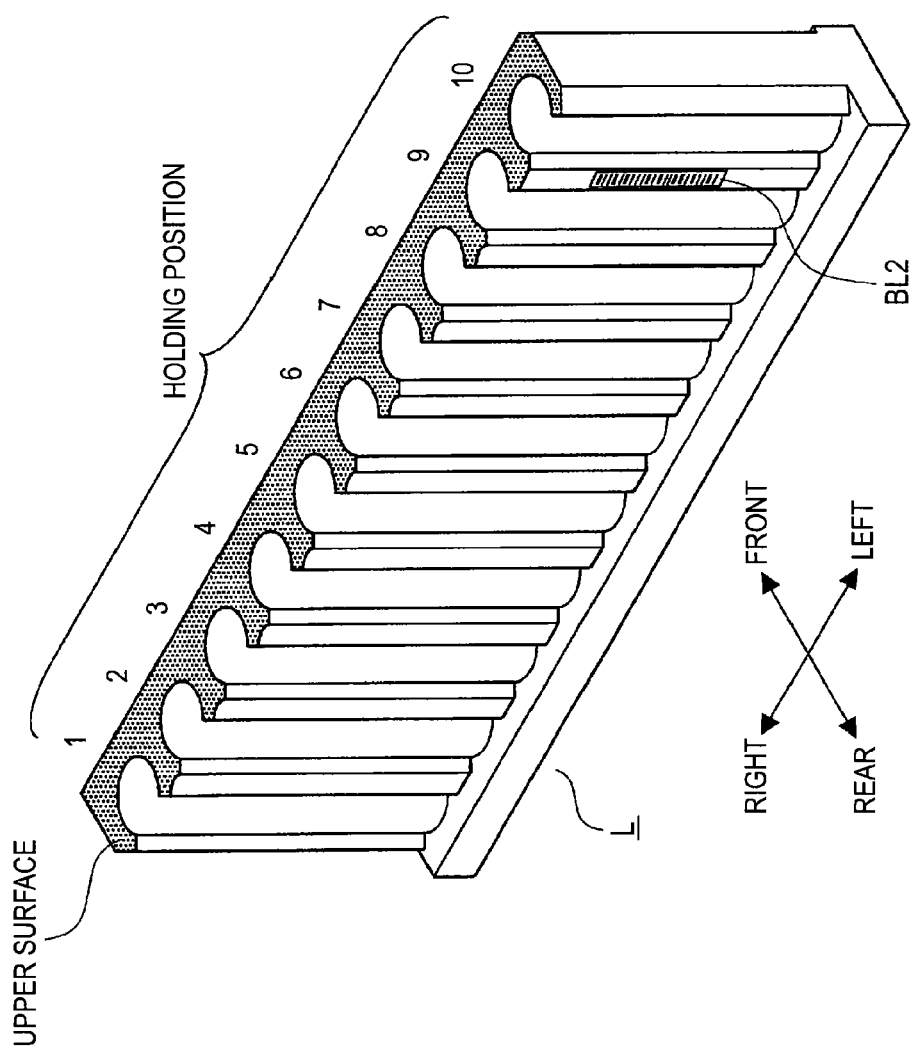

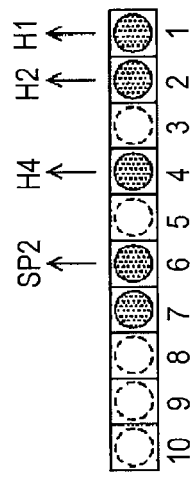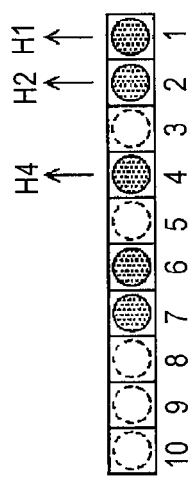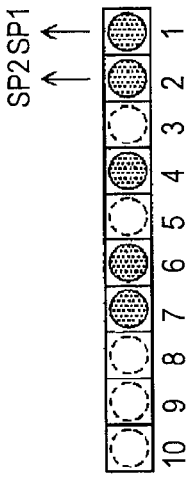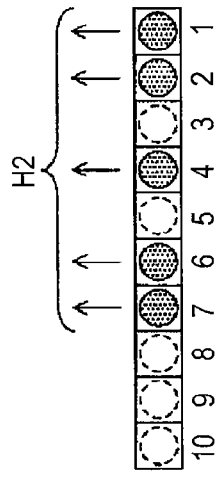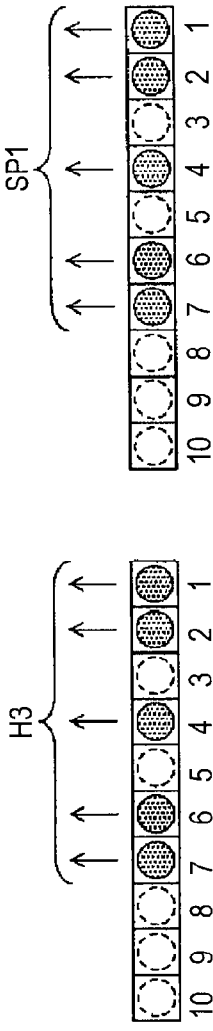

SAMPLE PROCESSING APPARATUS AND METHOD FOR TRANSPORTING RACK

RELATED APPLICATIONS

This application claims priority under 35 U.S.C. §119 to Japanese Patent Application No. 2010-121992 filed on May 27, 2010, the entire content of which is hereby incorporated by reference.

BACKGROUND OF THE INVENTION

1. Field of the Invention

The present invention relates to a sample processing apparatus which includes a plurality of sample processing units and a transport device transporting a rack capable of holding containers to the plurality of sample processing units, and a method for transporting a rack.

2. Description of the Related Art

Conventionally, there have been known a sample processing apparatus which transport a rack holding containers to a plurality of sample processing sections.

For example, in Japanese Patent Publication No. 2009/270869, there is disclosed an automatic analyzer which includes: a plurality of analysis units; a transport line transporting a rack which holds containers each containing a sample or a cleaning liquid to the analysis units; a rack supply section supplying a rack to the transport line; and a computer for overall management. In this automatic analyzer, the computer for overall management displays a setting screen for setting a transport destination of a rack in which a container containing a cleaning liquid is held. A user operates an operating section to set the transport destination of the rack via the setting screen before installing the rack in the automatic analyzer. After that, the rack is transported, by the transport line, to the analysis unit set as the transport destination.

However, in the automatic analyzer described in Japanese Patent Publication No. 2009/270869, a user is required to operate the operating section in order to set the analysis unit to be the transport destination of the rack via the setting screen. Accordingly, a bothersome work burden is imposed on the user.

The invention is contrived in view of the problem, and an object thereof is to provide a sample processing apparatus which can reduce the working burden on a user and a method for transporting a rack.

SUMMARY OF THE INVENTION

The scope of the invention is defined solely by the appended claims, and is not affected to any degree by the statements within this summary.

A first aspect of the present invention is a sample processing apparatus, comprising: a plurality of sample processing units each configured to process a sample; at least one transport device configured to provide a transport path along which a rack is transported to or from one of the plurality of sample processing units, wherein a rack comprises a plurality of positions configured to hold containers thereat, and at least some of the positions are correlated to at least some of the sample processing units; a controller comprising at least one processor and at least one memory that stores computer programs executed by the at least one processor to: direct the at least one transport device to transport the rack to deliver a container held therein to a sample processing unit correlated to a position of the container at which the container is held in the rack.

A second aspect of the present invention is a method for transporting a rack to or from one of a plurality of sample processing units through a transport path formed by at least one transport device, wherein a rack comprises a plurality of positions configured to hold containers thereat, the method comprising computer executable steps performed by a processor of a computer system to implement: determining a position of a container held in the rack, wherein at least some of the positions in the rack are correlated to at least some of the sample processing units; and directing the at least one transport device to transport the rack to deliver the container held therein to a sample processing unit correlated to the position of the container.

BRIEF DESCRIPTION OF THE DRAWINGS

FIG. 7 is a diagram showing the outline of the configurations of the transport unit, a measuring unit, and an information processing unit according to the embodiment;

FIG. 8 is a diagram showing the outline of the configurations of the transport unit and a smear preparation apparatus according to the embodiment;

FIG. 9 is a diagram showing the configuration of the rack ID of a special rack according to the embodiment;

FIGS. 10A and 10B are flowcharts showing a process in the transport controller according to the embodiment;

FIG. 11 is a diagram logically showing the information which is written onto a hard disk of the transport controller according to the embodiment;

FIG. 12 is a flowchart showing a process of "determining the transport destination of a special rack" according to the embodiment;

FIGS. 13A to 13G are diagrams explaining to which unit (apparatus) the container held in a special rack according to the embodiment is transported;

FIG. 18 is a diagram showing a rack of which the operation content can be identified by color of a modified example according to the embodiment; and FIGS. 19A to 19G are diagrams explaining to which unit (apparatus) the container held in a special rack is transported in a modified example of the sample processing apparatus according to the embodiment.

DETAILED DESCRIPTION OF THE PREFERRED EMBODIMENTS

This embodiment relates to a sample processing apparatus for performing examination and analysis relating to blood to which the invention is applied. The sample processing apparatus according to this embodiment includes three measuring units and one smear preparation apparatus. In the three measuring units, blood analysis is performed in parallel, and when it is necessary to prepare a smear based on the analysis result, the smear preparation apparatus prepares a smear.

Hereinafter, the sample processing apparatus according to this embodiment will be described with reference to the drawings.

Figure 1:
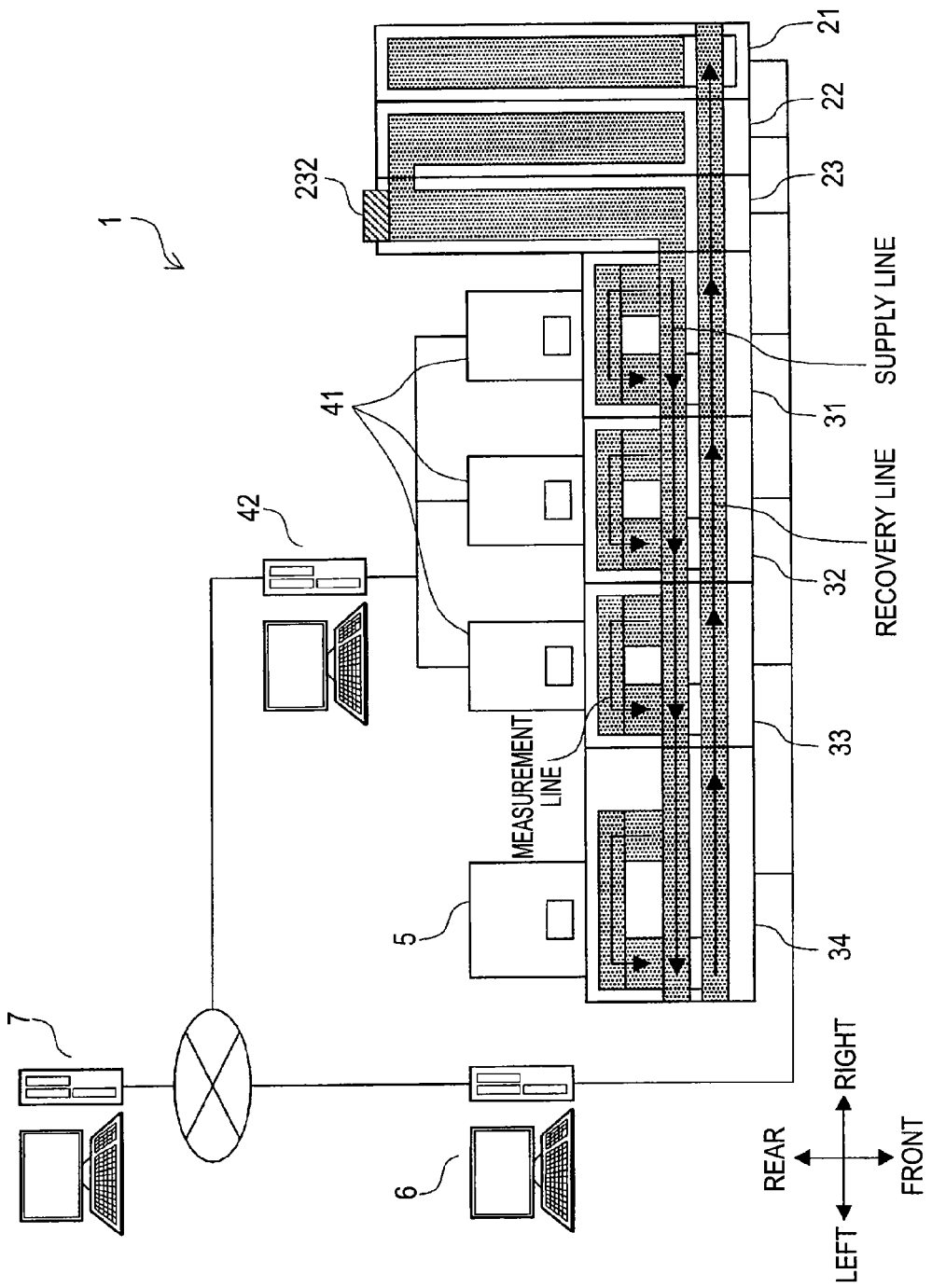
FIG. 1 is a plan view schematically showing the configuration when a sample processing apparatus according to an embodiment is viewed from the upper side.

FIG. 1 is a plan view schematically showing the configuration when a sample processing apparatus 1 is viewed from the upper side. The sample processing apparatus 1 includes a recovery unit 21, an insertion unit 22, an output unit 23, transport units 31 to 34, three measuring units 41, an information processing unit 42, a smear preparation apparatus 5, and a transport controller 6. In addition, the sample processing apparatus 1 according to this embodiment is connected to a host computer 7 via a communication network so as to communicate therewith.

The recover unit 21, the insertion unit 22, and the output unit 23 are each configured so as to be able to place a plurality of racks L capable of holding ten containers T therein.

Figure 2A:
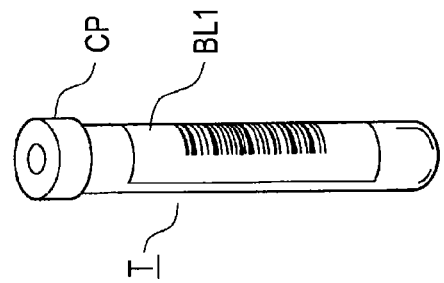
FIG. 2A is a view showing a container according to the embodiment.
Figure 2B:
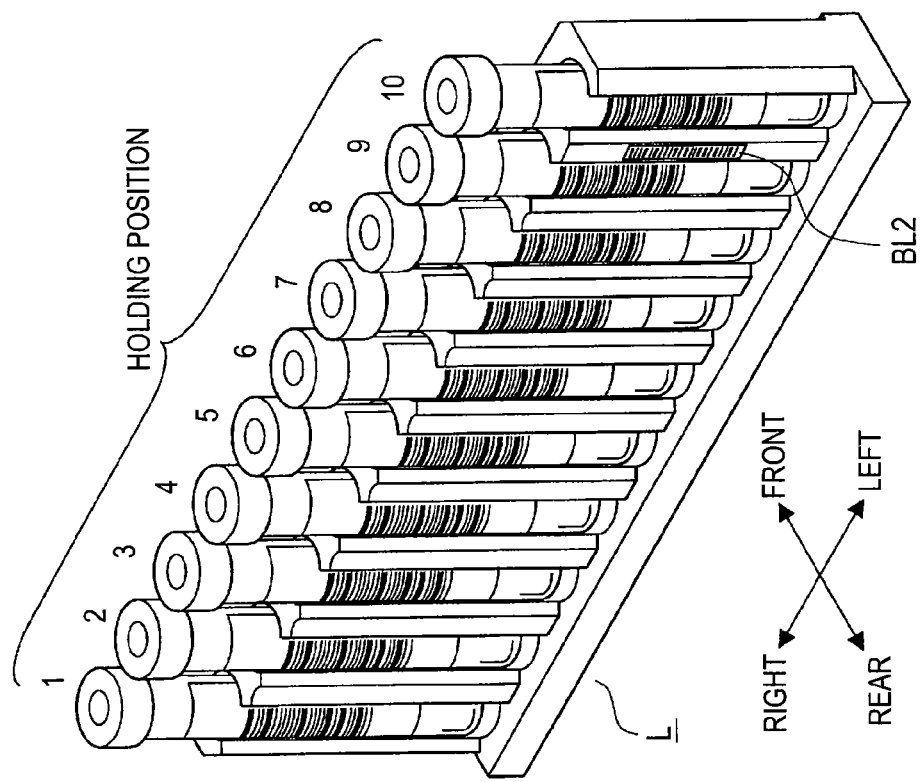
FIG. 2B is a view showing the configuration of a rack.

FIG. 2A is a perspective view showing the appearance of a container T. FIG. 2B is a perspective view showing the appearance of a rack L holding ten containers T. In FIG. 2B, the directions (the forward and backward, and rightward and leftward directions in FIG. 1) when the rack L is placed in the insertion unit 22 are also shown.

Referring to FIG. 2A, the container T is a tubular container made of glass or a synthetic resin having translucency and the upper end thereof is opened. A blood sample collected from a patient is contained therein and the opening at the upper end is sealed by a cap section CP. A barcode label BL1 is adhered to the side surface of the container T. A barcode showing a container ID is printed on the barcode label BL1.

Referring to FIG. 2B, in the rack L, ten holding sections are formed at holding positions 1 to 10 as shown in the drawing so as to hold ten containers T in parallel in a vertical state (erect state). In addition, a barcode label BL2 is adhered to the rear side surface of the rack L as shown in the drawing. A barcode showing a rack ID is printed on the barcode label BL2. The rack ID includes 6-digit information (letters, numbers, or symbols).

A cleaning liquid or an accuracy control sample (quality control sample) other than a sample may be contained in a container T. A container T containing a sample may be subjected to a first measurement and then may be subjected to a second or subsequent measurement. A case in which a cleaning liquid or an accuracy control sample (quality control sample) is contained in a container T and a case in which a sample (hereinafter, referred to as a "sample for re-examination") to be subjected to second or subsequent measurement is contained will be described later. Hereinafter, first, a case in which a sample (hereinafter, referred to as a "normal sample") to be subjected to a first measurement is contained in a container T and only containers T containing normal samples are held in a rack L will be described.

Returning to FIG. 1, the recover unit 21 accommodates racks L which are recovered through a recovery line to be described later. The insertion unit 22 accommodates racks L which are inserted by a user and outputs the accommodated racks L to the output unit 23. The output unit 23 includes a barcode reading section 232 for reading the rack ID of a rack L and the container ID of a container T. The barcode reading section 232 is provided with an optical sensor 232s (see FIG. 3) for detecting a container T. When a rack L output from the insertion unit 22 reaches a position at which a barcode is read by the barcode reading section 232, the presence or absence of a container T is detected by the optical sensor 232s, and then a rack ID is read out from a barcode label BL2 and a container ID is read out from a barcode label BL1. The read out rack ID is transmitted to the transport controller 6. In addition, the read out container ID is transmitted to the transport controller 6 in association with the holding position number of the container T. The rack ID of the rack L and the container IDs of the containers T associated with the holding positions in the rack L are collectively referred to as "rack information". In addition, the output unit 23 outputs a rack L in which the barcode reading has been completed to the transport unit 31. The holding positions 1 to 10 in the rack L are positioned at the optical sensor 232s in a predetermined order. Accordingly, through the presence or absence of the detection of the container T by the optical sensor 232s, it is possible to specify the holding position at which the container T is held.

The transport units 31 to 34 are connected to each other in the rightward-leftward direction so as to transfer racks L. The right end of the transport unit 31 is connected to the output unit 23 so as to transfer racks L. The transport units 31 to 33 are disposed in front of the three measuring units 41, respectively, as shown in the drawing, and the transport unit 34 is disposed in front of the smear preparation apparatus 5 as shown in the drawing.

As shown in the drawing, in the transport units 31 to 33, two transport lines are set for a case in which a rack L is transported to the corresponding measuring unit 41 and for a case in which the rack L is not transported. That is, when measurement is performed in the measuring unit 41, the rack L is transported along a "measurement line" shown by the rear U-shaped arrow. When measurement is not performed in the measuring unit 41 and measurement or preparation of a smear is performed on the downstream side (left side), the rack L is transported along a "supply line" shown by the intermediate left-pointing arrow so as to skip the above measuring unit 41. In addition, as shown in the drawing, in the transport units 31 to 33, a right-pointing transport line for transporting a rack L to the recovery unit 21 is set. That is, the rack L which is not required to be subjected to measurement or smear preparation on the downstream side (left side) is transported along the "recovery line" shown by the front right-pointing arrow and is recovered by the recovery unit 21. As in the transport units 31 to 33, in the transport unit 34, a measurement line, a supply line, and a recovery line are also set as shown in the drawing.

Each of the three measuring units 41 takes a container T from a rack L at a predetermined position on the measurement line of each of the transport units 31 to 33 which are respectively disposed in front of the measuring units, and measures a sample contained in this container T. That is, the measuring unit 41 moves the container T taken from the rack L to the inside of the measuring unit 41 and measures the sample which is contained in this container T. When the measurement in the measuring unit 41 is completed, the measuring unit 41 returns this container T to the original holding position in the rack L.

The information processing unit 42 is connected to the three measuring units 41 so as to communicate therewith and controls the operations of the three measuring units 41. In addition, the information processing unit 42 is connected to the host computer 7 so as to communicate therewith via a communication network and inquires the host computer 7 of a measurement order of a sample which is measured by the measuring unit 41. That is, when the container ID of a container T moved to the inside of the measuring unit 41 is read by a barcode reader 412 (see FIG. 7) in the measuring unit 41, the information processing unit 42 inquires the host computer 7 of the measurement order of this sample. After that, the information processing unit 42 controls the measurement operation of the measuring unit 41 based on the measurement order received from the host computer 7. In addition, the information processing unit 42 performs analysis based on the result of the measurement performed by the measuring unit 41.

The smear preparation apparatus 5 suctions a sample which is contained in a container T at a predetermined position on the measurement line in the transport unit 34 disposed in front of the smear preparation apparatus and prepares a smear of this sample. Whether a smear is prepared or not is determined by the transport controller 6 based on the result of the analysis which is performed by the information processing unit 42. When the transport controller 6 determines that the preparation of a smear is required, the rack L containing a sample to be a target is transported along the measurement line in the transport unit 34 and a smear is prepared in the smear preparation apparatus 5.

The transport controller 6 is connected to the recovery unit 21, the insertion unit 22, the output unit 23, and the transport units 31 to 34 so as to communicate therewith and controls the driving of the units. In addition, the transport controller 6 is connected to the host computer 7 so as to communicate therewith via a communication network. When receiving rack information from the output unit 23, the transport controller 6 inquires the host computer 7 of the measurement order. In addition, the transport controller 6 determines the transport destination of a rack L which is output from the output unit 23.

Figure 3:
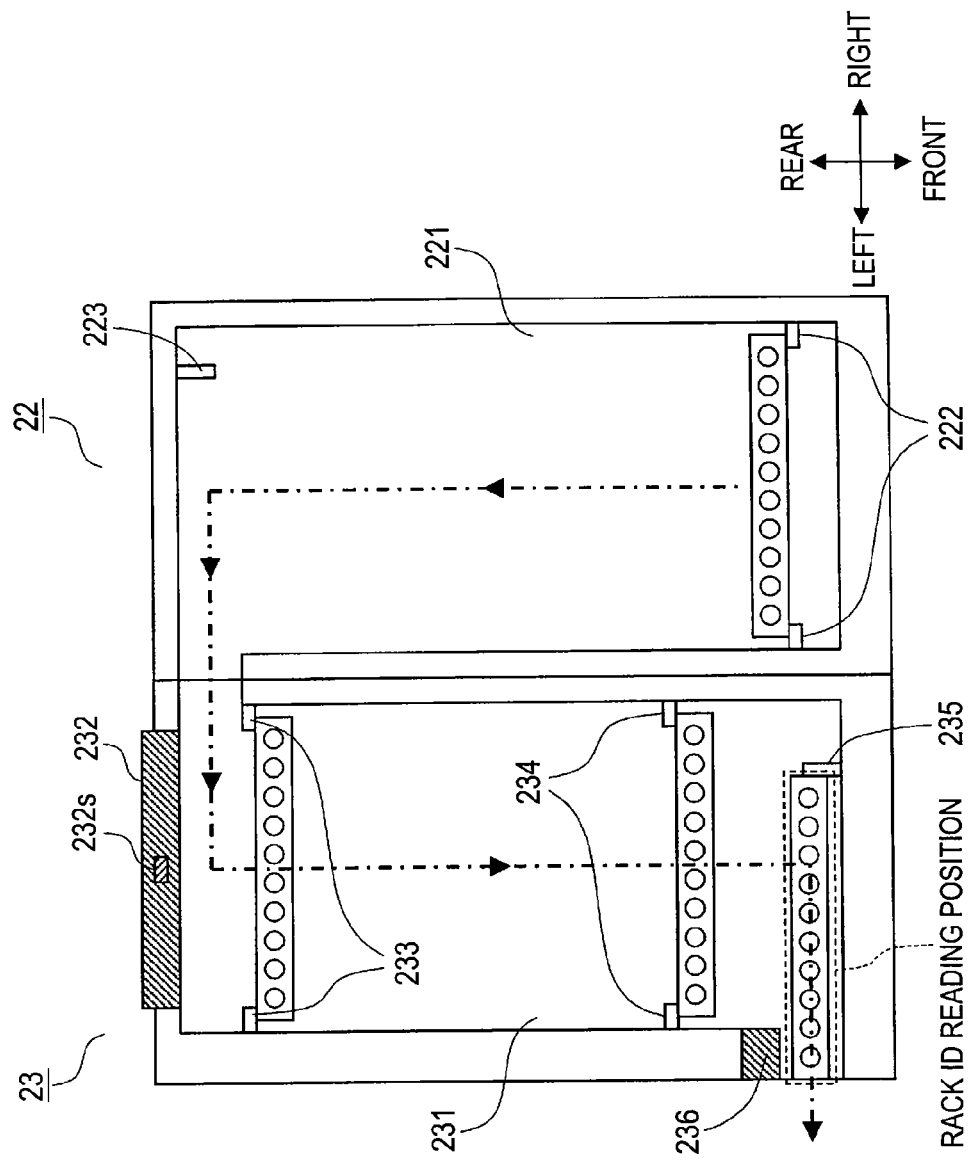
FIG. 3 is a plan view showing the configuration when an insertion unit and an output unit according to the embodiment are viewed from the upper side.

FIG. 3 is a plan view showing the configuration when the insertion unit 22 and the output unit 23 are viewed from the upper side. In the same drawing, the transport of a rack L in the rightward direction along the recovery line will be omitted in the drawing for the sake of convenience.

When a rack L is inserted onto a transport passage 221 in the insertion unit 22, rack input mechanisms 222 move backward while engaging with the front ends of the rack L and this rack L is sent to the rear of the transport passage 221. The rack L positioned at the rear of the transport passage 221 is output to the rear of a transport passage 231 in the output unit 23 when the right side surface of the rack L is pushed by a rack output mechanism 223. At the rear of the transport passage 231, rack information is read by the barcode reading section 232.

Next, the rack L positioned at the rear of the transport passage 231 is sent, by rack input mechanisms 233, to a position which moves forward by a width of the rack L in the forward-backward direction from the rear of the transport passage 231. Next, rack input mechanisms 234 move forward while engaging with the rear ends of the rack L and this rack L is sent to the front of the transport passage 231. The rack L positioned at the front of the transport passage 231 moves in the leftward direction when the right side surface of the rack L is pushed by a rack output mechanism 235.

In this case, when the rack L moves slightly to the left side from the front of the transport passage 231 and the barcode label BL2 of the rack L is positioned in front of a barcode reading section 236, the rack ID is read by the barcode reading section 236. Hereinafter, the position of the rack L at this point is referred to as a "rack ID reading position". When the rack ID is read by the barcode reading section 236, the output unit 23 transmits this rack ID and an output request to the transport controller 6. Based on the received rack ID, the measuring unit 41 or the smear preparation apparatus 5 to be a transport destination of this rack L is decided by the transport controller 6. After that, the rack L which is positioned at the rack ID reading position is further pushed out in the leftward direction by the rack output mechanism 235 to be output to the transport unit 31.

Figure 4:
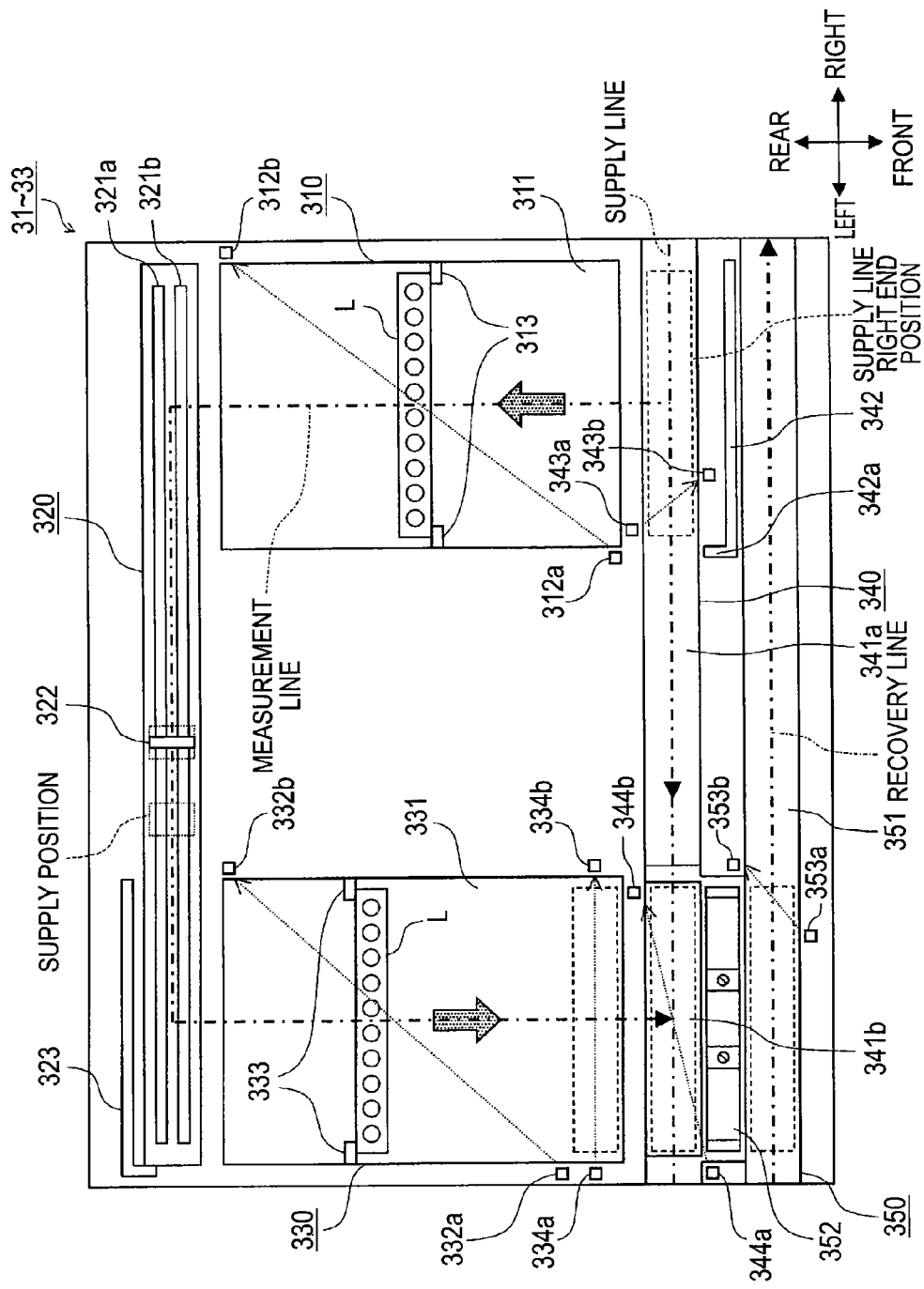
FIG. 4 is a plan view showing the configuration when a transport unit according to the embodiment is viewed from the upper side.

FIG. 4 is a plan view showing the configuration when the transport units 31 to 33 are viewed from the upper side. The transport units 31 to 33 have a right table 310, a rack transport section 320, a left table 330, and rack transport sections 340 and 350. The measurement line in FIG. 1 is constituted by the right table 310, the rack transport section 320, and the left table 330. In addition, the supply line in FIG. 1 is constituted by the rack transport section 340 and the recovery line in FIG. 1 is constituted by the rack transport section 350. The transport units 31 to 33 have the same configuration.

When the measurement of a rack L output from the upstream side (right side) is not performed in the measuring unit 41 corresponding to this transport unit, this rack L is linearly sent by belts 341*a* and 341*b* of the rack transport section 340 from the right end of the rack transport section 340 to the left end along the supply line. Transmission-type sensors 344*a* and 344*b* are installed in the vicinity of the left end of the rack transport section 340. By the sensors 344*a* and 344*b*, the rack L which is positioned at the left end of the rack transport section 340 is detected.

Next, when the measurement of the rack L output from the upstream side (right side) is performed in the measuring unit 41 corresponding to this transport unit, this rack L is positioned at the right end of the rack transport section 340. That is, a rack pushing mechanism 342 moves backward so that a wall section 342*a* slightly protrudes on the supply line from the state shown in the drawing. In this manner, the rack L output from the upstream side collides with the wall section 342*a* and stops. In addition, transmission-type sensors 343*a* and 343*b* are installed in the vicinity of the right end of the rack transport section 340. By the sensors 343*a* and 343*b*, the rack L which is positioned at the right end of the rack transport section 340 is detected.

Next, due to further backward movement of the rack pushing mechanism 342, this rack L is pushed out to the front end of a transport passage 311 of the right table 310. When transmission-type sensors 312*a* and 132*b* detect the rack L on the transport passage 311, rack input mechanisms 313 move backward while engaging with the front ends of the rack L and the rack L is sent to the back. When the rack L is sent up to the right end of the rack transport section 320, belts 321*a* and 321*b* are driven and the rack L is sent in the leftward direction.

After that, the rack L arrives at the position of a container sensor 322. The container sensor 322 is a contact-type sensor. When a container T held in the rack L passes through the position straight under the container sensor 322, the contact piece of the container sensor 322 is bent by the container T and thus the presence of the container T is detected.

At a supply position positioned on the left side of the position at which the container T has been detected by the container sensor 322, by a distance corresponding to two sample containers T, a hand section (not shown) of the measuring unit 41 grips the container T and takes the sample container T from the sample rack L. The removed container T returns to the rack L after being used in the measurement in the measuring unit 41. While the container T returns to the rack L, the transport of the rack L is on hold.

In this manner, when the processing of all the containers T to be processed in the measuring unit 41 corresponding to this transport unit is completed among the containers T held in the rack L, the rack L is sent up to the left end of the rack transport section 320 by the belts 321*a* and 321*b*. After that, the rack L is pushed out to the rear end of a transport passage 331 of the left table 330 by a rack pushing mechanism 323. When transmission-type sensors 332*a* and 332*b* detect the rack L on the transport passage 331, rack input mechanisms 333 move forward while engaging with the rear ends of the rack L. Therefore, the rack L is sent to the front.

Transmission-type sensors 334*a* and 334*b* are installed in the vicinity of the front of the left table 330. By the sensors 334*a* and 334*b*, the rack L which is positioned at the front of the left table 330 is detected.

Next, a partition section 352 which is in front of the left table 330 and is between the rack transport sections 340 and 350 is controlled to be opened and closed and the rack L is positioned in either of the rack transport sections 340 or 350.

When any container T held in the rack L is required to be subjected to processing such as measurement in the smear preparation apparatus 5 or the measuring unit 41 on the downstream side, the rack L moves to the left end of the rack transport section 340 by the rack input mechanisms 333 in a state in which the rack transport sections 340 and 350 are partitioned by the partition section 352. After that, this rack L is output to the transport unit on the downstream side by the belts 341*b* of the rack transport section 340.

On the other hand, when any container T held in the rack L is not required to be subjected to processing such as measurement in the smear preparation apparatus 5 or the measuring unit 41 on the downstream side, the upper surface of the partition section 352 is dropped to be disposed at the same height as the upper surface of the belt 341*b* of the rack transport section 340 and the rack L moves up to the left end of the rack transport section 350 by the rack input mechanisms 333. In this manner, by the rack input mechanisms 333, the rack L is moved across the rack transport section 340 from the left table 330 up to the left end of the rack transport section 350. The rack L which is positioned at the left end of the rack transport section 350 is detected by transmission-type sensors 353*a* and 353*b* which are installed in the vicinity of the left end of the rack transport section 350. After that, this rack L is moved in the rightward direction along the recovery line by a belt 351 of the rack transport section 350. The rack L which is transported along the recovery line is accommodated in the recovery unit 21.

The transport unit 34 has a barcode reader 343 (see FIG. 8) which is installed in the vicinity of the right end of the rack transport section 320 in addition to the same configuration as those of the transport units 31 to 33. When a rack L containing a sample in which it is determined that the preparation of a smear is required is transported to the transport unit 34, this rack L is transported along the measurement line. At this time, the container ID of the container T held in the rack L is read by the barcode reader 343 before arriving at the supply position. When the container T is positioned at the supply position, the sample is suctioned from the container T and the smear preparation apparatus 5 prepares a smear. After that, this rack L is transported in the rightward direction toward the recovery unit 21 along the recovery line.

Figure 5:
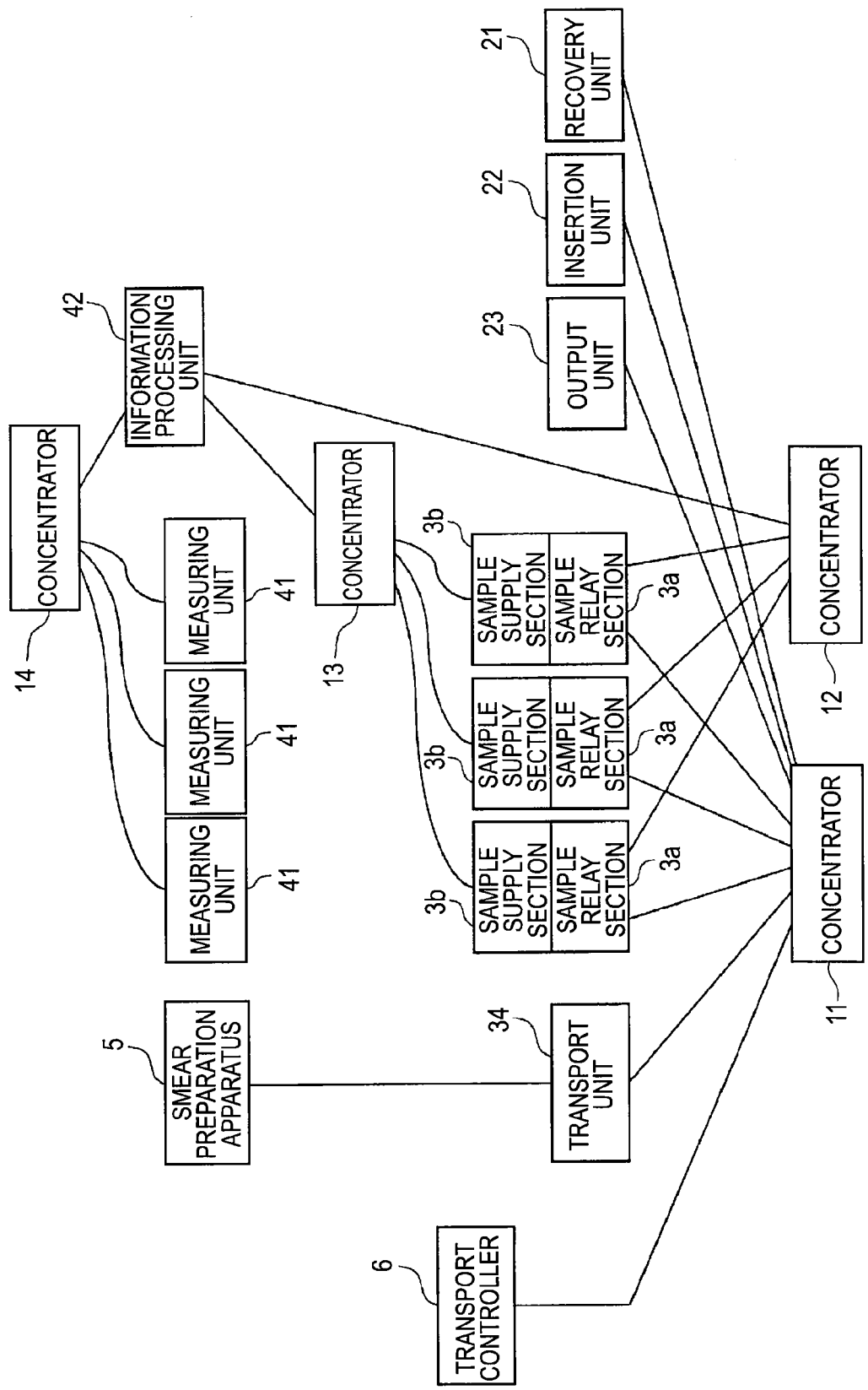
FIG. 5 is a diagram schematically showing the mutual connection relationships between each unit (apparatus) in the sample processing apparatus according to the embodiment.

FIG. 5 is a diagram schematically showing the mutual connection relationships between the units (apparatuses) in the sample processing apparatus 1.

Here, in the drawing, the transport units 31 to 33 are divided into a sample relay section 3*a* and a sample supply section 3*b*, respectively. In greater detail, the sample relay section 3*a* includes the left table 330 and the rack transport sections 340 and 350 of FIG. 4, and one of the neighboring two transport units receives and transports a rack L to the other transport unit. The sample supply section 3*b* includes the right table 310 and the rack transport section 320 of FIG. 4 and transports a rack L to the supply position in order to measure a sample by the measuring unit 41.

The recovery unit 21, the insertion unit 22, the output unit 23, the three sample relay sections 3*a*, the transport unit 34, and the transport controller 6 are connected to a concentrator 11 so as to communicate therewith. The three sample relay sections 3*a* and the information processing unit 42 are connected to a concentrator 12 so as to communicate therewith. The three sample supply sections 3*b* and the information processing unit 42 are connected to a concentrator 13 so as to communicate therewith. The three measuring units 41 and the information processing unit 42 are connected to a concentrator 14 so as to communicate therewith.

Figure 6:
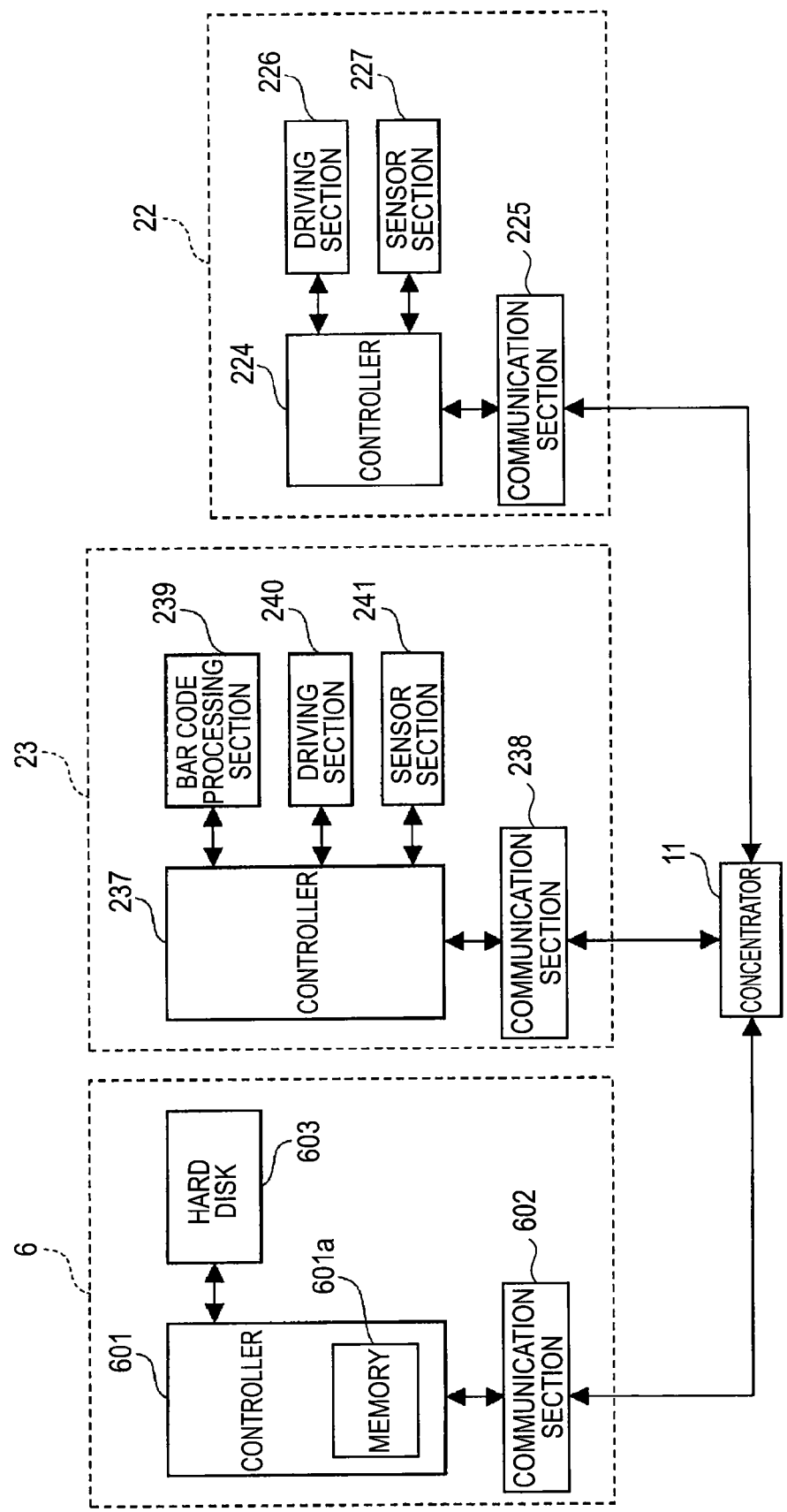
FIG. 6 is a diagram showing the outline of the configurations of a transport controller, the output unit, and the insertion unit according to the embodiment.

FIG. 6 is a diagram showing the outline of the configurations of the transport controller 6, the output unit 23, and the insertion unit 22.

The transport controller 6 includes a controller 601, a communication section 602, and a hard disk 603. In addition, the controller 601 includes a memory 601*a*.

The controller 601 controls other units (apparatuses) by executing a computer program stored in the memory 601*a* or the hard disk 603. The memory 601*a* is used to read out computer programs stored on the hard disk 603 and is also used as a working area when these computer programs are executed. Not only the controller 601, but also the controllers of other units (apparatuses) to be described later have a memory.

The communication section 602 includes a communication interface for performing data communication with an external apparatus based on Ethernet (registered trade name) standards to perform data communication with the concentrator 11. On the hard disk 603, computer programs for controlling other units (apparatuses) are stored. In addition, on the hard disk 603, a computer program for determining a transport destination of the rack L which is output from the output unit 23 and a computer program for deciding the smear preparation apparatus 5 or the measuring unit 41 corresponding to the holding position in the rack L to be described later are stored. In addition, on the hard disk 603, the rack information received from the output unit 23 and the measurement order inquiring at the host computer 7 are stored.

The output unit 23 includes a controller 237, a communication section 238, a barcode processing section 239, a driving section 240, and a sensor section 241.

The controller 237 controls the sections in the output unit 23 by executing a computer program stored in a memory (not shown) in the controller 237 according to the controller 601 of the transport controller 6. The communication section 238 performs data communication with the concentrator 11 as in the communication section 602 of the transport controller 6.

The barcode processing section 239 includes the barcode reading sections 232 and 236 shown in FIG. 3. The barcode information read by the barcode processing section 239 is output to the controller 237. The driving section 240 includes a mechanism for transporting a rack L which is accommodated in the output unit 23 and a stepping motor for driving this mechanism. The sensor section 241 includes a sensor for detecting a rack L which is accommodated in the output unit 23. The sensor section 241 outputs a detection signal to the controller 237.

As shown in the drawing, the insertion unit 22 has a configuration in which the bar-code processing section 239 is removed from the output unit 23. The recovery unit 21 (not shown) also has the same configuration as that of the insertion unit 22.

FIG. 7 is a diagram showing the outline of the configurations of the transport unit 31, the measuring unit 41 and the information processing unit 42. In the same drawing, for the sake of convenience, only one transport unit 31 and only one measuring unit 41 are shown. However, the transport units 32 and 33 and the other measuring units 41 also have the same configurations.

The transport unit 31 has a configuration in which a communication section 302b, a driving section 303b, and a sensor section 304b are added to the insertion unit 22 of FIG. 6.

A communication section 302a performs data communication with the concentrators 11 and 12 and the communication section 302b performs data communication with the concentrator 13 as in the communication section 302a. A driving section 303a is controlled by a controller 301 and the driving section 303b is controlled by the information processing unit 42 via the communication section 302b. A sensor section 304a outputs a detection signal to the controller 301 and the sensor section 304b outputs a detection signal to the information processing unit 42 via the communication section 302b.

The communication section 302b, the driving section 303b, and the sensor section 304b are included in the sample supply section 3b of FIG. 5 and the sections in the transport unit 31 other than the communication section 302b, the driving section 303b, and the sensor section 304b are included in the sample relay section 3a of FIG. 5. The driving section 303a and the sensor section 304a include mechanisms for transporting and detecting racks L on the left table 330 and the rack transport sections 340 and 350 of FIG. 4, respectively. The driving section 303b and the sensor section 304b include mechanisms for transporting and detecting racks L on the right table 310 and the rack transport section 320 of FIG. 4, respectively.

The measuring unit 41 includes a communication section 411, the barcode reader 412, a driving section 413, and a sensor section 414. As in the communication section 302b of the transport unit 31, the communication section 411 performs data communication with the concentrator 14. The barcode reader 412 is installed in the measuring unit 41 and reads the container ID of a container T. The driving section 413 and the sensor section 414 include mechanisms for transporting a container T in the measuring unit 41 and measuring a sample contained in the container T, respectively.

The information processing unit 42 has the same configuration (the hard disk and the memory are not shown) as that of the transport controller 6 of FIG. 6. Via a communication section 422 and the concentrator 13, a controller 421 controls the driving section 303b of the transport unit 31 and receives a detection signal of the sensor section 304b. In addition, via the communication section 422 and the concentrator 14, the controller 421 controls the driving section 413 of the measuring unit 41 and receives a container ID read by the barcode reader 412 and a detection signal of the sensor section 414.

FIG. 8 is a diagram showing the outline of the configurations of the transport unit 34 and the smear preparation apparatus 5. The transport unit 34 has a configuration in which the barcode reader 343 is added to the insertion unit 22 of FIG. 6. The smear preparation apparatus 5 has the same configuration as that of the insertion unit 22 of FIG. 6. The transport unit 34 includes a controller 341, a communication section 342, the barcode reader 343, a driving section 344, and a sensor section 345. The smear preparation apparatus 5 includes a controller 501, a communication section 502, a driving section 503, and a sensor section 504.

The communication section 342 of the transport unit 34 performs data communication with the concentrator 11. The communication section 342 is connected to the communication section 502 of the smear preparation apparatus 5 by a signal line and also performs data communication with the communication section 502. When receiving a smear preparation instruction from the transport unit 34 via the communication section 502, the controller 501 of the smear preparation apparatus 5 suctions a sample from a container T at the supply position on the measurement line of the transport unit 34 and prepares a smear.

Here, as described above, there may be not only a case in which only containers T containing a normal sample are held, but also a case in which only containers T containing a cleaning liquid, an accuracy control sample (quality control sample), or a sample for re-examination may be held in the rack L of this embodiment. The cleaning liquid is a liquid which is used in cleaning of predetermined sites in the measuring unit 41 and the smear preparation apparatus 5. The accuracy control sample (quality control sample) is a specimen which is prepared so as to obtain a predetermined measurement result. The specimen is used to determine whether a desired measurement result is obtained when the measurement is performed in the measuring unit 41 as in the case of a normal sample. The measurement accuracy of the measuring unit 41 in which the measurement has been performed is found by comparing a measurement result of the accuracy control sample (quality control sample) with the desired measurement result.

In this embodiment, independently of racks L (hereinafter, referred to as "normal racks") which hold only containers T containing a normal sample, racks L (hereinafter, referred to as "racks for cleaning") which hold only containers T containing a cleaning liquid, racks L (hereinafter, referred to as "racks for accuracy control (quality control) measurement") which hold only containers T containing an accuracy control sample (quality control sample), and racks L (hereinafter, referred to as "racks for re-examination") which hold containers T containing a sample for re-examination are provided. These racks L have the same shape of that of a normal rack.

As in the case of a normal rack, when the rack for cleaning, the rack for accuracy control (quality control) measurement, and the rack for re-examination (hereinafter, these three racks are collectively referred to as a "special rack") are output from the output unit 23, the transport controller 6 decides between the smear preparation apparatus 5 and the measuring unit 41 to be a transport destination. The transport controller 6 controls the transport units 31 to 34 so as to transport this rack to the decided transport destination.

When a rack for cleaning is transported to the measuring unit 41 or the smear preparation apparatus 5 which is a transport destination, a cleaning liquid is suctioned from a container T containing the cleaning liquid which is held in this rack for cleaning, and cleaning is performed in the transport destination. When a rack for accuracy control (quality control) measurement is transported to the measuring unit 41 which is a transport destination, an accuracy control sample (quality control sample) is suctioned from a container T containing the accuracy control sample (quality control sample) which is held in this rack for accuracy control (quality control) measurement, and measurement of the accuracy control sample (quality control sample) is performed. When a rack for re-examination is transported to the measuring unit 41 or the smear preparation apparatus 5 which is a transport destination, the measurement is performed in the same manner as in the case of a normal sample in the transport destination.

FIG. 9 is a diagram showing the configuration of the rack ID of a special rack.

As shown in the drawing, the rack L having a rack ID in which "SR" is in the upper two digits is used as a special rack. The rack L having a rack ID of which the upper two digits are not "SR" is used as a normal rack.

Any one of "S", "R", "Q", and "N" is written in the third digit from the top of the rack ID of the special rack. When "S" is written in this digit, this special rack is used as a rack for cleaning (hereinafter, referred to as a "rack for shutdown cleaning") which shuts the unit (apparatus) down after the cleaning operation. When "R" is written in this digit, this special rack is used as a rack for cleaning (hereinafter, referred to as a "rack for normal cleaning") which does not shut the unit (apparatus) down after the cleaning operation (the unit is made to be on hold). When "Q" or "N" is written in this digit, this special rack is used as a rack for accuracy control (quality control) measurement or a rack for re-examination.

Any one of "H", "S", and "A" is written in the third digit from the bottom of the rack ID of the special rack. When "H" is written in this digit, the transport target of this special rack is only the measuring unit. When "S" is written in this digit, the transport target of this special rack is only the smear preparation apparatus. The transport target of the special rack in which "A" is written in this digit is all the units (the measuring unit and the smear preparation apparatus).

Any one of the numbers "00" to "09" are written in the lower two digits of the rack ID of the special rack. When "00" is written in this digit, the unit (apparatus) to be a transport destination of the container T which is held in this special rack is determined according to the holding position of each container T. When any one of "01" to "09" are written in the lower two digits of the rack ID of the special rack, the unit (apparatus) to be a transport destination of the container T is determined according to this number.

Next, the transport control of a rack L will be described with reference to FIGS. 10A, 10B, and 17.

Referring to FIG. 10A, the controller 601 of the transport controller 6 holds a process until the rack ID, which is read by the barcode reading section 232 at the rear end of the transport passage 231 of the output unit 23, and the container IDs (rack information) of the containers T, which are associated with the holding positions in the rack L, are received from the output unit 23 (S11). When receiving the rack information (S11: YES), the controller 601 stores the received rack information on the hard disk 603 of the transport controller 6 (S12).

FIG. 11 is a diagram logically showing the information which is written on the hard disk 603 of the transport controller 6. As shown in the drawing, the rack information received in S11 of FIG. 10A includes the rack ID and the container IDs corresponding to the respective holding positions in this rack L and is written on the hard disk 603. In the example of FIG. 11, containers T are not held in the holding positions 3 and 5 to 11.

Returning to FIG. 10A, next, it is determined whether this rack L is a normal rack or a rack for re-examination based on the rack information received in S11 (S13). The controller 601 determines whether this rack L is a normal rack or a special rack with reference to the upper two digits of the rack ID as shown in FIG. 9 and determines whether this rack L is a rack for shutdown cleaning, a rack for normal cleaning, a rack for accuracy control (quality control) measurement, or a rack for re-examination with reference to the third digit from the top.

When this rack L is a normal rack or a rack for re-examination (S13: YES), the controller 601 inquires the host computer 7 of the measurement data of the containers T containing a sample which are held in this rack L (S14). On the other hand, when this rack L is not a normal rack nor a rack for re-examination, that is, when this rack L is a rack for cleaning or a rack for accuracy control (quality control) measurement (S13: NO), the process returns to S11.

When inquiring the host computer 7 of the measurement orders (S14), the controller 601 holds the process until the measurement orders are received from the host computer 7 (S15). When receiving the measurement orders from the host computer 7 (S15: YES), the controller 601 stores the received measurement orders on the hard disk 603 of the transport controller 6 together with the rack information (S16) and the process returns to S11.

The measurement orders received in S14 are written in association with the containers T containing a sample as shown in FIG. 11. In the example of FIG. 11, the measurement orders for the containers T in the holding positions 1, 2, and 4 are written.

In this manner, in the transport controller 6, the processes of S11 to S16 of FIG. 10A are repeated for each rack L.

Referring to FIG. 10B, the controller 601 of the transport controller 6 holds the process until an output request including the rack ID which is read by the barcode reading section 236 at the rack ID reading position in the transport passage 231 of the output unit 23 is received (S21). When receiving the output request including the rack ID (S21: YES), the controller 601 reads out the rack information stored in S12 of FIG. 10A and the measurement orders stored in S16 based on the received rack ID (S22). When this rack L is neither a normal rack nor a rack for re-examination, the measurement orders are not stored and thus only the rack information is read out.

Next, the controller 601 determines whether or not this rack L is a special rack (S23). When this rack L is a special rack (S23: YES), the controller 601 performs a process of "determining the transport destination of the special rack" (S24). The process of "determining the transport destination of the special rack" will be described later with reference to FIG. 12. On the other hand, when this rack L is not a special rack, that is, a normal rack (S23: NO), the controller 601 decides the smear preparation apparatus 5 or the measuring unit 41 to be a transport destination according to the measurement orders corresponding to the respective containers T which are held in this normal rack (S25).

Next, the controller 601 transmits an instruction to the output unit 23 so as to output this rack L to the transport unit 31 from the rack ID reading position of FIG. 3 (S26) and the process returns to S21.

In S24 or S25, the transport destination is determined for each held container T and is written for each held container T as shown in FIG. 11. In the example of FIG. 11, the transport destinations of the containers T in the holding positions 1, 2, and 4 are written.

In this manner, in the transport controller 6, the processes of S21 to S26 of FIG. 10B are repeated for each rack L.

FIG. 12 is a flowchart showing the process of "determining the transport destination of the special rack".

The controller 601 of the transport controller 6 determines a transport target group (see FIG. 9) with reference to the third digit from the bottom of the rack ID which is received in addition to the output request in S21 of FIG. 10B (S101). Next, the controller 601 determines whether the lower two digits of the rack ID are "00" or not (S102).

When the lower two digits of the rack ID are "00" (S102: YES), the controller 601 determines the transport destination of a container T which is held in this special rack according to the holding position of the container T (S103). In greater detail, when the units (apparatuses) in the transport target group are represented by U1, U2, U3, . . . in order from the upstream side (right side in FIG. 1) in the transport direction, the transport destinations of the containers T which are held in the holding positions 1, 2, 3, . . . are U1, U2, U3, . . . , respectively.

On the other hand, when the lower two digits of the rack ID are not "00" (S102), the controller 601 determines the transport destination of a container T which is held in this special rack according to the number of the lower two digits of the rack ID (S104). In greater detail, when the units (apparatuses) in the transport target group are represented by U1, U2, U3, . . . in order from the upstream side (right side in FIG. 1) in the transport direction, the transport destination of all the containers T which are held in this special rack is the unit (apparatus) corresponding to the number of the lower two digits of the rack ID (U1 is determined if this number is 01, U2 is determined if this number is 02, . . . , and U10 is determined if this number is 10).

In this manner, the process of "determining the transport destination of the special rack" ends.

Here, the hard disk 603 of the transport controller 6 stores in advance information about the arrangement order of the units (apparatuses) from the upstream side and information for specifying the units (apparatuses) (hereinafter, referred to as "configuration information"). The controller 601 of the transport controller 6 reads out and deploys the configuration information in the memory 601a when being started up, and as shown in the above-described S103 and S104, the controller determines the transport destination according to the holding position of a container T or the lower two digits of the rack ID.

The rack L which is output from the output unit 23 is transported by the transport units 31 to 34 so that the container T in each holding position is processed in the transport destination. At this time, the transport units 31 to 34 transport the rack L according to the controller 601 of the transport controller 6 and transmit the transport position of the rack L which is detected by the plurality of sensors shown in FIG. 4 to the transport controller 6. When the transported rack L is positioned at the supply line right end position of the transport unit positioned in front of the unit (apparatus) which is the transport destination, this rack L is pushed out to the right table 310 by the rack pushing mechanism 342. The process after the pushing out of the rack L to the right table 310 will be described later with reference to FIGS. 14 to 17.

FIGS. 13A to 13G are diagrams explaining to which unit (apparatus) the container T held in a special rack is transported. Here, as shown in FIG. 13A, for the sake of convenience, the three measuring units 41 shown in FIG. 1 are designated H1, H2, and H3 from the right side, and the smear preparation apparatus 5 is designated SP1. FIGS. 13B to 13G are diagrams showing the transport destination of a container T when the rack ID is set as shown in the respective diagrams. In addition, as shown in FIGS. 13B to 13G, containers T are held in the holding positions 1, 2, 4, 6, and 7 in each special rack.

FIG. 13B is a diagram showing a case in which the rack ID is "SRRA00". In this case, from the rack ID, it is found that this rack L is a rack for normal cleaning, the transport targets of the containers T which are held are all the units (apparatuses), and the transport destination is determined according to the holding position of the container T. Accordingly, the transport destinations of the containers T containing a cleaning liquid which are held in the holding positions 1, 2, and 4 are determined as H1, H2, and SP1, respectively. Since no container T is held in the holding position 3 corresponding to H3, the rack L is not transported to H3. Here, since there are no units (apparatuses) corresponding to the holding positions 6 and 7, the containers T which are held in the holding positions 6 and 7 are not transported to any unit (apparatus).

FIG. 13C is a diagram showing a case in which the rack ID is "SRRH00". In this case, from the rack ID, it is found that this rack L is a rack for normal cleaning, the transport targets of the containers T which are held are only the measuring units, and the transport destination is determined according to the holding position of the container T. Accordingly, the transport destinations of the containers T containing a cleaning liquid which are held in the holding positions 1 and 2 are determined as H1 and H2, respectively. Since the transport targets are only the measuring units (three units) in this case, only the three holding positions 1, 2, and 3 from the right side in the rack L are holding positions effective in determining the transport targets. Accordingly, the containers T which are held in the holding positions 4, 6, and 7 are not transported to any unit (apparatus).

FIG. 13D is a diagram showing a case in which the rack ID is "SRRS00". In this case, from the rack ID, it is found that this rack L is a rack for normal cleaning, the transport target of the containers T which are held is only the smear preparation apparatus, and the transport destination is determined according to the holding position of the container T. Accordingly, the transport destination of the container T which is held in the holding position 1 is determined as SP1. Since the transport target is only the smear preparation apparatus (one apparatus) in this case, only the one holding position 1 from the right side in the rack L is a holding position effective in determining the transport target. Accordingly, the containers T which are held in the holding positions 2, 4, 6, and 7 are not transported to any unit (apparatus).

FIG. 13E is a diagram showing a case in which the rack ID is "SRSA02". In this case, from the rack ID, it is found that this rack L is a rack for shutdown cleaning, the transport targets of the containers T which are held are all the units (apparatuses), and the transport destination of this rack L is the second unit (apparatus) in the transport targets since the lower two digits of the rack ID are "02". Accordingly, the transport destination of all the containers T which are held in the rack L is determined as H2. In this case, the shutdown is performed by the cleaning liquid which is contained in the last container T held in the rack L after cleaning. That is, the cleaning liquids in the containers T are used in cleaning in order of the holding positions 7, 6, 4, 2, and 1, and after the cleaning liquid in the container T in the holding position 1 is used in cleaning, H2 is shut down.

FIG. 13F is a diagram showing a case in which the rack ID is "SRQH03". In this case, from the rack ID, it is found that this rack L is a rack for accuracy control (quality control) measurement, the transport targets of the containers T which are held are only the measuring units, and the transport destination is the third unit (apparatus) in the transport targets. Accordingly, the transport destination of all the containers T which are held in the rack L is determined as H3.

FIG. 13G is a diagram showing a case in which the rack ID is "SRNS01". In this case, from the rack ID, it is found that this rack L is a rack for re-examination, the transport target of the containers T which are held is only the smear preparation apparatus, and the transport destination is the first unit (apparatus) in the transport targets. Accordingly, the transport destination of all the containers T which are held in the rack L is determined as SP1.

Figure 14B:
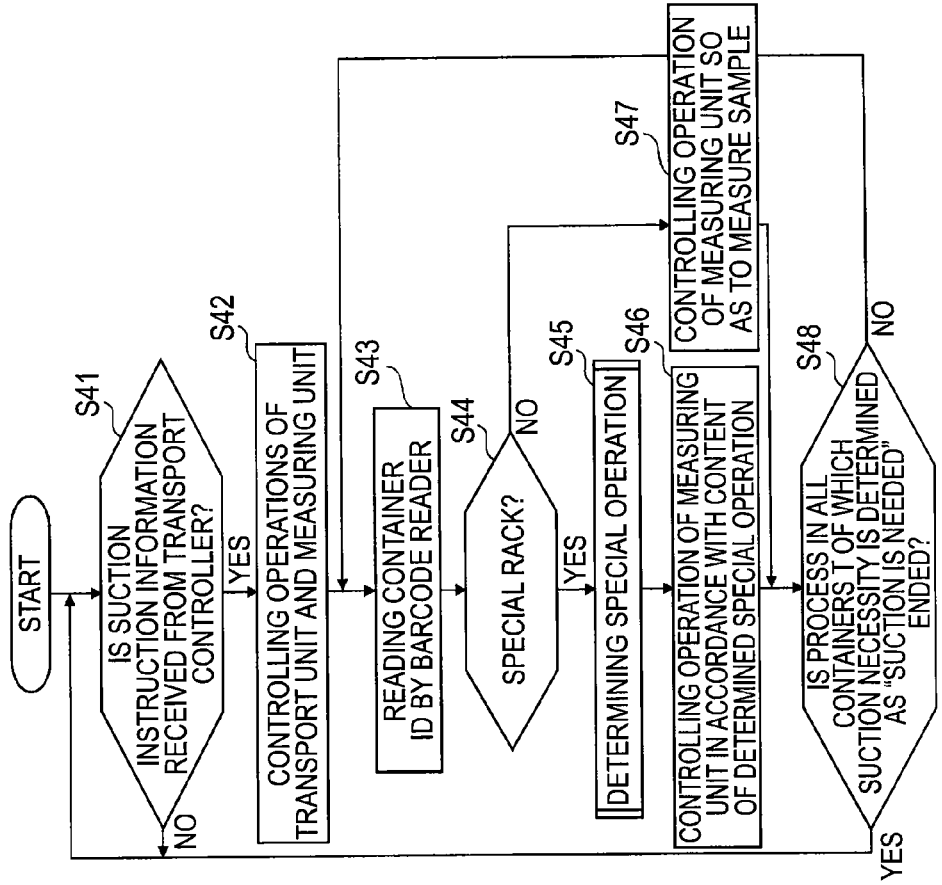
FIG. 14B is a flowchart showing a process in the information processing unit.
Figure 14A:
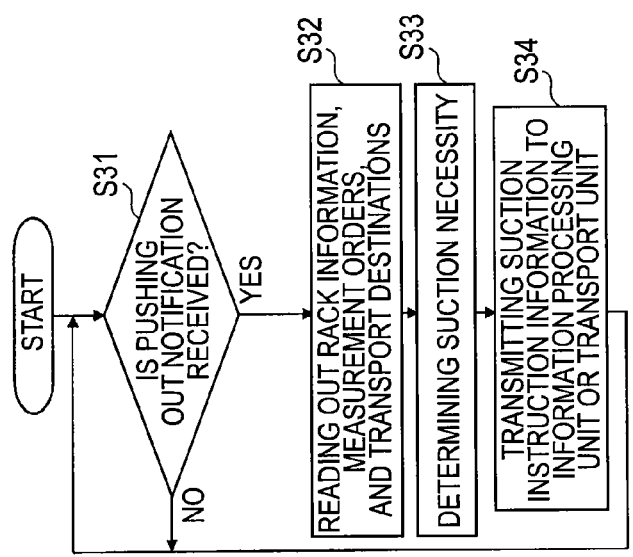
FIG. 14A is a flowchart showing a process in the transport controller according to the embodiment.

FIG. 14A is a flowchart showing a process in the transport controller 6.

As described above, when a rack L is positioned at the supply line right end position of the transport unit corresponding to the unit (apparatus) which is a transport destination, the rack is pushed out to the right table 310. At this time, the transport unit transmits a notification (hereinafter, referred to as a "pushing out notification") indicating that the rack L is pushed out to the right table 310 to the transport controller 6.

When receiving the pushing out notification (S31: YES), the controller 601 of the transport controller 6 reads out the rack information, the measurement orders, and the transport destinations of the rack L pushed out to the right table 310 from the hard disk 603 (S32).

Next, the controller 601 determines information (hereinafter, referred to as "suction necessity") of whether the suction from a container T is performed by the unit (apparatus) corresponding to the transport unit transmitting the pushing out notification (S33). Regarding the suction necessity, when the transport destination of each container T matches the unit (apparatus) corresponding to the transport unit transmitting the pushing out notification, "the suction is needed", and when the transport destination does not match the unit (apparatus) corresponding to the transport unit transmitting the pushing out notification, "the suction is not needed".

Referring to FIG. 11, the rack L shown in the drawing is pushed out to the right table 310 of the transport unit 31 corresponding to H2 (the second measuring unit 41 from the right side). At this time, only the transport destination of the container T which is held in the holding position 2 is H2. Accordingly, "the suction is needed" in the holding position 2, and "the suction is not needed" in the holding position other than the holding position 2.

Returning to FIG. 14A, next, the controller 601 transmits a suction instruction to the information processing unit 42 or the transport unit 34 (S34). In greater detail, when receiving the pushing out notification from the transport units 31 to 33, the controller 601 transmits a suction instruction to the information processing unit 42, and when receiving the pushing out notification from the transport unit 34, the controller transmits suction instruction information to the transport unit 34. The suction instruction information includes the rack information of the rack L and the suction necessity of the container T in each holding position. Here, the suction necessity of the container T in each holding position is determined according to the determination in Step S33. In addition, when this rack L is a normal rack or a rack for re-examination, the suction instruction information includes the measurement order associated with the container T.

In the transport controller 6, the processes of S31 to S34 are repeated for each reception of the pushing out notification.

FIG. 14B is a flowchart showing the process in the information processing unit 42.

When receiving the suction instruction information from the transport controller 6 (S41: YES), the controller 421 of the information processing unit 42 controls the operations of the transport unit which is a source of this suction instruction information and in which the rack L is positioned and the measuring unit 41 corresponding to this transport unit (S42).

When the rack L is transported along the measurement line and the container T, of which the suction necessity included in the suction instruction is determined as "the suction is needed", moves to the inside of the measuring unit 41, the controller 421 reads the container ID of the container T moved to the inside of the measuring unit 41 by the barcode reader 412 (see FIG. 7) (S43).

Next, the controller 421 determines whether or not the rack L holding this container T is a special rack with reference to the rack ID which is included in the suction instruction information received in S41 (S44). When the rack L is a special rack (S44: YES), the controller 421 performs a process of "determining the special operation" (S45) and controls the operation of the measuring unit 41 according to the content of the special operation determined by the process of "determining the special operation" (will be described later with reference to FIG. 17) (S46). On the other hand, when the rack L is not a special rack, that is, a normal rack (S44: NO), the operation of the measuring unit 41 is controlled so as to measure the sample which is contained in this container T (S47).

Next, the controller 421 determines whether or not the process has ended in all the containers T of which the suction necessity is determined as "the suction is needed" and which are held in the rack L (S48). When the process has ended in all the containers T (S48: YES), the process returns to S41. On the other hand, when the process has not ended in all the containers T (S48: NO), the processes of S43 to S47 are performed until the process in all the containers T ends.

In this manner, the controller 421 repeats the processes of S41 to S48 for each reception of the suction instruction information from the transport controller 6.

Figure 15B:
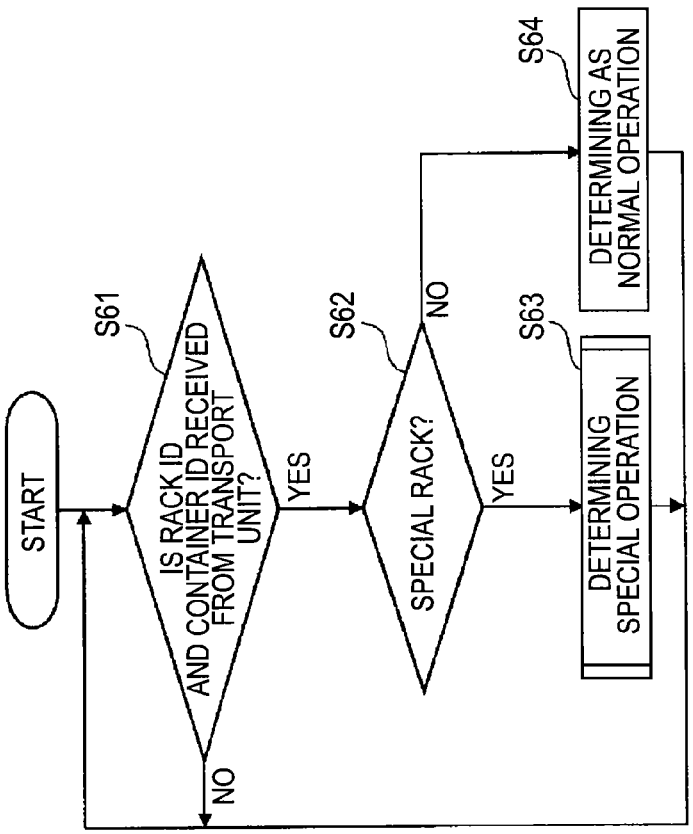
FIG. 15B is a flowchart showing a process in the smear preparation apparatus.
Figure 15A:
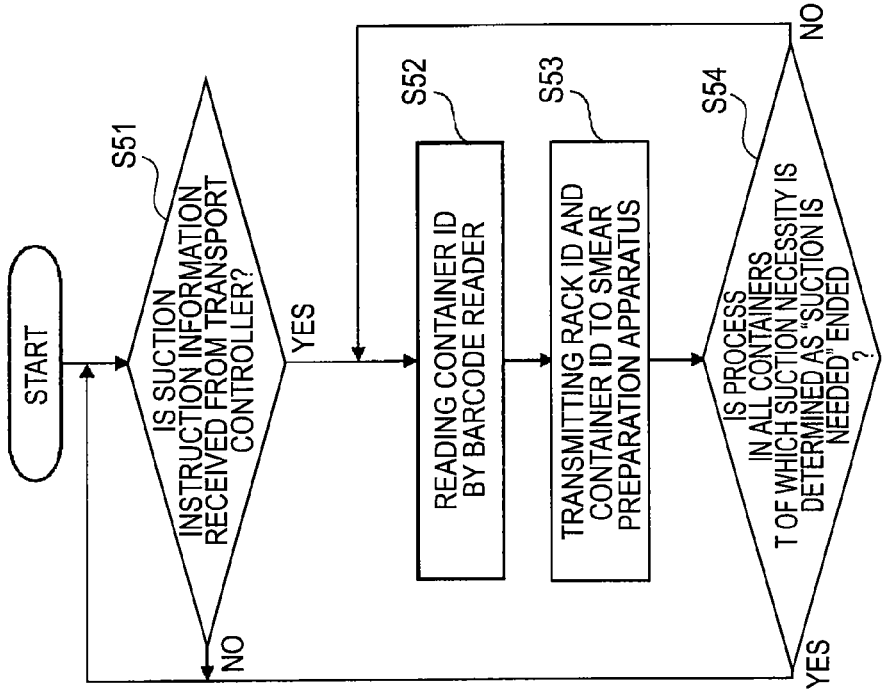
FIG. 15A is a flowchart showing a process in the transport unit according to the embodiment.

FIG. 15A is a flowchart showing the process in the transport unit 34.

When receiving the suction instruction information from the transport controller 6 (S51: YES), the controller 341 of the transport unit 34 controls the units in the transport unit 34 to transport the rack L which is a source of this suction instruction information along the measurement line.

When the container T of which the suction necessity included in the suction instruction information is determined as "the suction is needed" is positioned in front of the barcode reader 343 (see FIG. 8), the controller 341 reads the container ID of this container T by the barcode reader 343 (S52). The controller 341 transmits the rack ID which is included in the suction instruction and the container ID which is read in S52 to the smear preparation apparatus 5 (S53).

Next, the controller 341 determines that the process has ended in all the containers T of which the suction necessity is determined as "the suction is needed" and which are held in the rack L (S54). When the process has ended in all the containers T (S54: YES), the process returns to S51. On the other hand, when the process has not ended in all the containers T (S54: NO), the processes of S52 and S53 are performed until the process in all the containers T ends.

In this manner, the controller 341 repeats the processes of S51 to S54 for each reception of the suction instruction information from the transport controller 6.

FIG. 15B is a flowchart showing the process in the smear preparation apparatus 5.

When receiving the rack ID and the container ID from the transport unit 34 (S61: YES), the controller 501 of the smear preparation apparatus 5 determines whether or not this rack L is a special rack (S62). When this rack L is a special rack (S62: YES), the process of "determining the special operation" (will be described later with reference to FIG. 17) is performed (S63), and when this rack L is not a special rack, that is, a normal rack (S62: NO), the content of the operation for the rack L is determined as an operation for normal smear preparation (S64) and the process returns to S61.

Figure 16B:
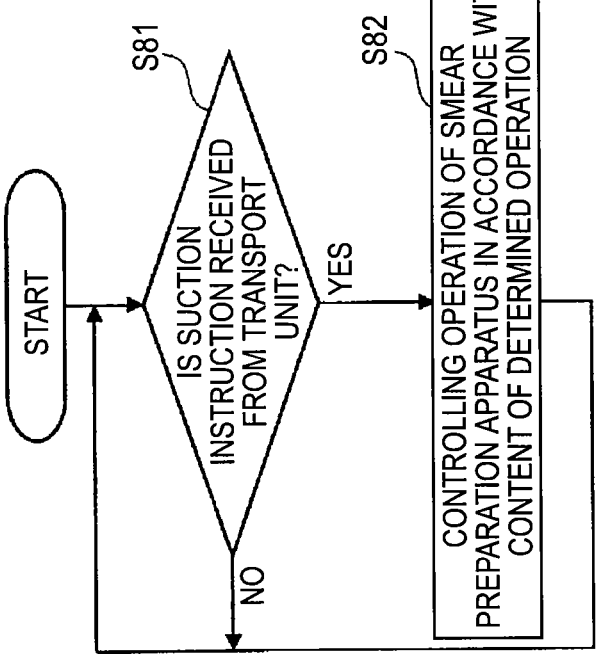
FIG. 16B is a flowchart showing a process in the smear preparation apparatus.
Figure 16A:
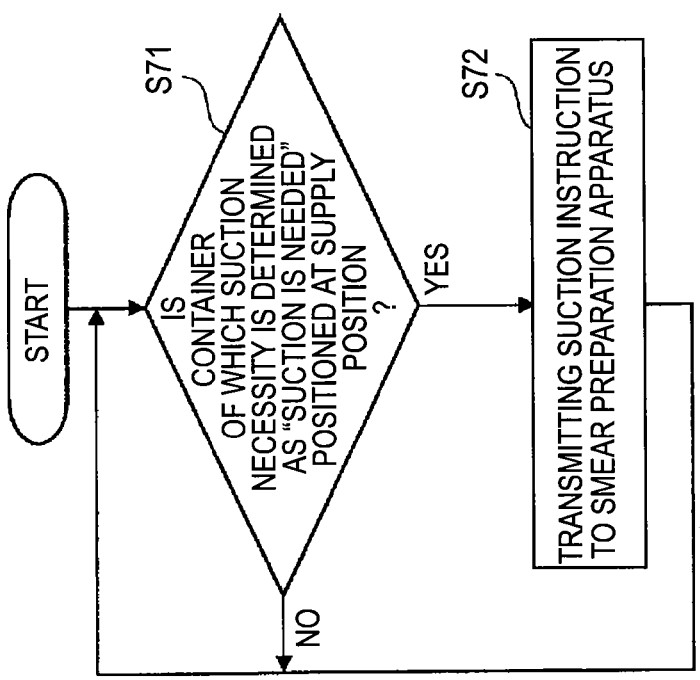
FIG. 16A is a flowchart showing a process in the transport unit according to the embodiment.

FIG. 16A is a flowchart showing the process in the transport unit 34.

When determining that the container T of which the suction necessity is determined as "the suction is needed" is positioned at the supply position (S71: YES), the controller 341 of the transport unit 34 transmits the suction instruction to the smear preparation apparatus 5 so as to perform the suction in this container T (S72) and the process returns to S71.

FIG. 16B is a flowchart showing the process in the smear preparation apparatus 5.

When receiving the suction instruction from the transport unit 34 (S81: YES), the controller 501 of the smear preparation apparatus 5 controls the operation of the smear preparation apparatus 5 according to the content of the operation which is determined in S63 or S64 of FIG. 15B (S82). That is, when performing the special operation, the controller 501 controls the operation of the smear preparation apparatus 5 so that the liquid in the container T positioned at the supply position is suctioned and the determined special operation is performed using this liquid. In addition, when performing the normal operation, the controller controls the operation of the smear preparation apparatus 5 so that the sample in the container T positioned at the supply position is suctioned and a smear is prepared. After that, the process returns to S81.

Figure 17:
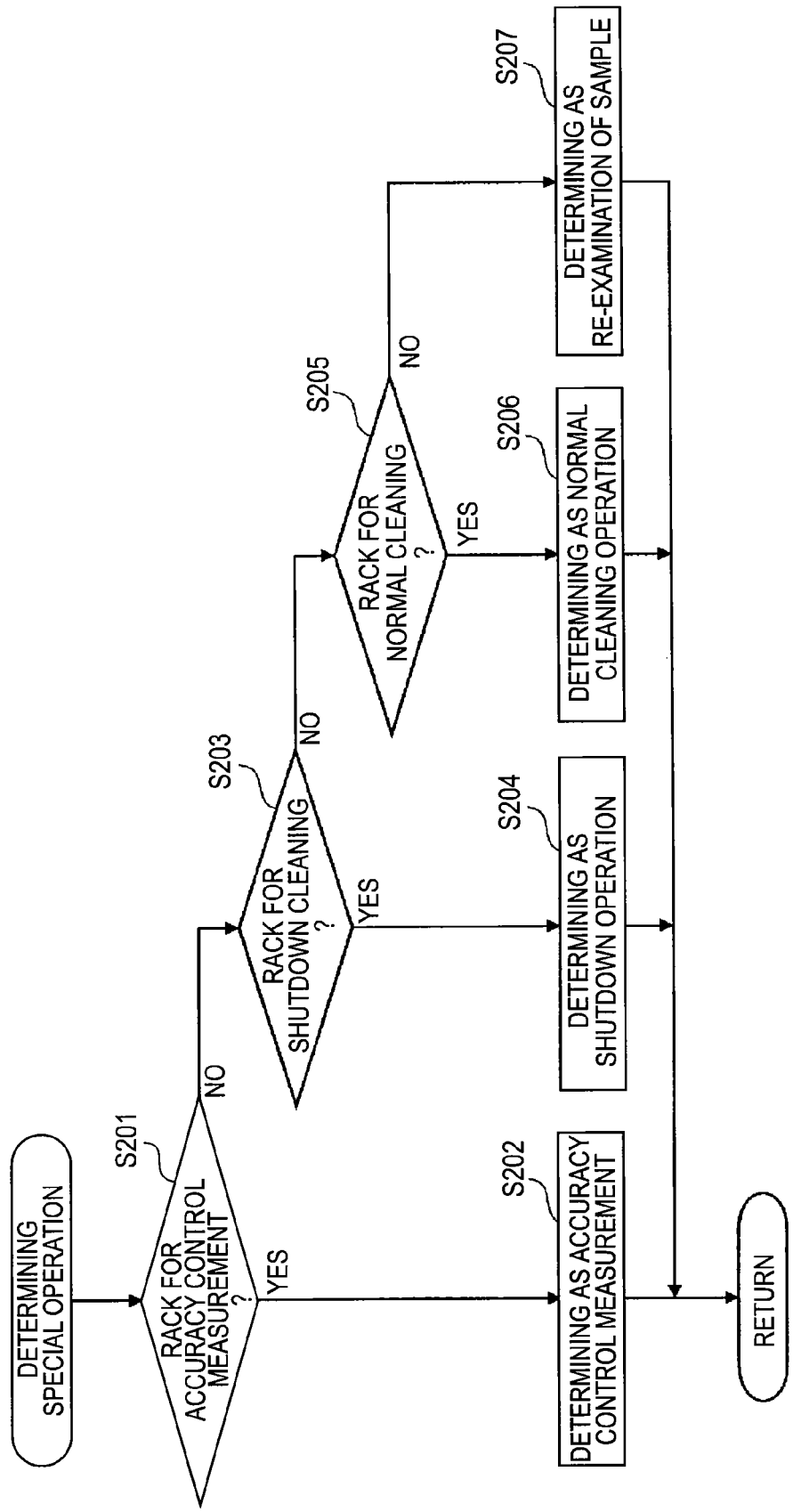
FIG. 17 is a flowchart showing a process of "determining a special operation" according to the embodiment.

FIG. 17 is a flowchart showing the process of "determining the special operation". This process is performed by the controller 421 of the information processing unit 42 in S45 of FIG. 14B, and is performed by the controller 501 of the smear preparation apparatus 5 in S63 of FIG. 15B.

When determining that this rack L is a rack for accuracy control (quality control) measurement with reference to the rack ID (S201: YES), the controller which performs the process of "determining the special operation" determines the content of the special operation of the container T which is held in this rack L as the accuracy control measurement (S202).

When determining that this rack L is not a rack for accuracy control measurement (S201: NO) but is a rack for shutdown cleaning (S203: YES), the controller determines the content of the special operation of the container T which is held in this rack L as an operation (shutdown operation) of shutting down the measuring unit 41 or the smear preparation apparatus 5 after the cleaning operation (S204).

When determining that this rack L is not a rack for shutdown cleaning (S203: NO) but is a rack for normal cleaning (S205: YES), the controller determines the content of the special operation of the container T which is held in this rack L as a normal cleaning operation (S206).

When determining that this rack L is not a rack for normal cleaning, that is, this rack L is a rack for re-examination (S205: NO), the controller determines the content of the special operation of the container T which is held in this rack L as a re-examination of the sample (S207).

In this manner, the process of "determining the special operation" ends.

According to this embodiment, when a container T is held in a special rack, the unit (apparatus) which is a transport destination is determined according to the holding position of the held container T. Accordingly, simply by setting the container T in the holding position in the rack L, a user can transport the container T to the unit (apparatus) corresponding to the holding position which is set.

In addition, according to this embodiment, as shown in FIGS. 13A to 13G, since the holding positions of the containers T which are held in a rack L and the order of the arrangement of the units are associated with each other, a user can visually and intuitively grasp the transport destination of the container T.

In addition, according to this embodiment, the transport destination according to the holding position is determined based on the configuration information of the unit (apparatus). Accordingly, even when the arrangement of the units (apparatuses) is changed, it is possible to easily modify the association between the holding position of the container T and the unit (apparatus) which is a transport destination simply by changing the configuration information.

As described above, the embodiments of the invention have been described, but the embodiments of the invention are not limited thereto.

For example, in the above-described embodiments, blood is exemplified as a measurement target. However, urine can also be a measurement target. That is, the invention can also be applied to a sample processing system examining urine and a clinical sample processing system examining other clinical samples.

In addition, in the above-described embodiments, when the units (apparatuses) in the transport target group are represented by U1, U2, U3, . . . in order from the upstream side (right side in FIG. 1) of the transport direction, the holding positions 1, 2, 3, . . . are associated with U1, U2, U3, . . . , respectively, but the invention is not limited thereto. The holding positions 10, 9, 8, . . . may be associated with U1, U2, U3, . . . , respectively.

In addition, in the above-described embodiments, the controller 421 of the information processing unit 42 controls the operations of the measuring units 41, but the invention is not limited thereto. The controller 601 of the transport controller 6 may directly control the operations of the measuring units 41.

In addition, in the above-described embodiments, the rack L is identified by the rack ID which is read out from the barcode label BL2 adhered to the rack L, but the invention is not limited thereto. The rack L may be identified by the radio frequency identification (RFID) tag, the shape of the rack L, the color of the rack L, or the like. In addition, by the container ID which is read out from the barcode label BL1 adhered to the container T, the rack L may be identified which holds this container T.

The special rack may be allowed to hold information that the rack is a special rack and information for causing a user to identify the content of the operation which is performed in the special rack. For example, the color, mark, or the like according to the content of the operation which is performed in the special rack may be given to the special rack.

FIG. 18 is a diagram showing a rack L in which the operation content can be identified by color.

As shown in the drawing, the upper surface of the rack L is colored. When this rack L is a rack for shutdown cleaning, is a rack for normal cleaning, is a rack for accuracy control measurement, and is a rack for re-examination, the color applied to the upper surface is, for example, yellow, blue, green, and red, respectively. In this manner, a user can visually identify the content of the special operation which is executed in the transport destination when the special rack is transported to the transport destination. As shown in the same drawing, in place of the application of a color to the upper surface of the rack L, a seal showing the special operation content may be adhered to the upper surface of the rack L.

In addition, in the above-described embodiments, the sample processing apparatus 1 includes the three measuring units 41 and the one smear preparation apparatus 5, but the invention is not limited thereto. The sample processing apparatus 1 may include four or more measuring units and two or more smear preparation apparatuses.

FIGS. 19A to 19G are diagrams explaining to which unit (apparatus) the container T held in a special rack L is transported when the sample processing apparatus 1 includes four measuring units and two smear preparation apparatuses. In this case, in the sample processing apparatus 1, measuring units H1, H2, H3, and H4 and smear preparation apparatuses SP1 and SP2 are arranged in order from the right side as shown in FIG. 19A. Also in this case, as in the above-described embodiments, the transport destination of each container T is determined from the rack ID and the holding position of the container T as shown in FIGS. 19B to 19G.

In addition, in the above-described embodiments, the process of "determining the special operation" is performed by the controller 421 of the information processing unit 42 and the controller 501 of the smear preparation apparatus 5, but the invention is not limited thereto. The above process may be performed by the controller 601 of the transport controller 6. In this case, the content of the special operation which is determined by the controller 601 may be included in the suction instruction information.

In addition, in the above-described embodiments, the transport controller 6 performs the process of determining the transport destination of a rack L and the process of controlling the rack transport operation by the recovery unit 21, the insertion unit 22, the output unit 23, and the transport units 31 to 34. However, another controller may perform the process of determining the transport destination of the rack L.

In addition, in the above-described embodiments, it may be determined whether or not the container ID is associated with the type of the rack L before the suction operation of the measuring units 41 and the smear preparation apparatus 5 is performed. In this manner, for example, when a container T containing a liquid other than a cleaning liquid is held in a rack for cleaning, when a container T containing a liquid other than a quality control sample is held in a rack for accuracy control measurement, and when a container T containing a liquid other than a sample is held in a rack for re-examination and a normal rack, the suction can be stopped (skipped).

In addition, in the above-described embodiments, based on information about the order of the arrangement of the units (apparatuses) from the upstream side and information (configuration information) for specifying the units (apparatuses), the transport destination according to the holding position is determined as shown in S103 and S104 of FIG. 12. However, the invention is not limited thereto. The association relationship between the holding position and the unit (apparatus) may be stored on the hard disk 603 of the transport controller 6 and the transport destination according to the holding position may be determined based on the association relationship.

In addition, in the above-described embodiments, the container T containing a sample for re-examination is transported by using a rack for re-examination, but the invention is not limited thereto. A container T containing a sample for re-examination may be held in a normal rack. In this case, the fact that the operation on the above normal rack is a re-examination is set by a user via, for example, the transport controller 6, the information processing unit 42, or another computer. In this manner, the setting that the operation content is re-examination is required for the user, but since the transport destination is determined by the holding position of the container T as in the above-described embodiments, a work burden on the user can be reduced. Similarly, a container T containing a cleaning liquid or a quality control sample may be held in a normal rack and the content (normal cleaning, shutdown after cleaning, accuracy control) of the operation on the above normal rack may be set by a user.

The embodiments of the invention can be appropriately and variously modified within the scope of the technical idea shown in the claims.

What is claimed is:

1. A sample processing apparatus, comprising:
   a plurality of sample processing units each configured to process a sample, wherein the sample processing units includes at least first and second sample processing units;
   at least one transport device configured to provide a transport path along which a rack is transported to or from one of the plurality of sample processing units, wherein a rack comprises a plurality of positions configured to hold containers thereat, and at least some of the positions are correlated to at least some of the sample processing units;
   a controller comprising at least one processor and at least one memory that stores computer programs executed by the at least one processor to:
   obtain identification information from a rack;
   recognize a presence or absence of a container with respect to each of the plurality of positions on the rack, when the obtained identification information corresponds to a special rack;
   if a first container is present in a first position of the rack, determine the first sample processing unit to be a transport destination of the first container in accordance with recognizing the presence of the first container in the first position of the rack, and direct the at least one transport device to transport the rack to deliver the first container to the first sample processing unit; and
   if a second container is present in a second position of the rack, determine the second sample processing unit to be a transport destination of the second container in accordance with recognizing the presence of the second container in the second position of the rack, and direct the at least one transport device to transport the rack to deliver the second container to the second sample processing unit.

2. The sample processing apparatus according to claim 1, wherein the at least some of the positions in the rack are correlated to positions along the transport path of the at least some of the sample processing units.

3. The sample processing apparatus according to claim 1, wherein the at least some of the positions in the rack are lined in an order correlated to an order in which the at least some of the sample processing units are positioned along the transport path.

4. The sample processing apparatus according to claim 3, wherein the orders of the at least some of the positions in the rack and the positions of the at least some of the sample processing units are defined similarly by sequential numbers counted from upstream towards downstream of the transport path, and correlations between the at least some of the positions in the rack and the positions of the at least some of the sample processing units are established by same numbers of the orders.

5. The sample processing apparatus according to claim 1, wherein after directing the at least one transport device to transport the rack to deliver the first container to the first sample processing unit, the controller directs the at least one transport device to transport the rack from the first sample processing unit to deliver the second container to the second sample processing unit.

6. The sample processing apparatus according to claim 1, wherein the container may contain one of a sample for retesting, a cleaning liquid and a control sample.

7. The sample processing apparatus according to claim 1, wherein the at least one memory stores a program executable by the processor to direct the at least one transport device to transport the rack to a sample processing unit correlated to the rack.

8. The sample processing apparatus according to claim 1, wherein the at least one memory stores a program executable by the processor to direct a sample processing unit to perform, on a sample in a container to be delivered to the sample processing unit, processing of a type determined by a type of a rack which holds the container.

9. The sample processing apparatus according to claim 8, wherein the special rack is of a type holding a container containing a cleaning liquid, and the processor directs the sample processing unit to perform cleaning using the cleaning liquid.

10. The sample processing apparatus according to claim 8, wherein the special rack is of a type holding a container containing a control sample, and the processor directs the sample processing unit to perform a quality control measurement, using the control sample.

11. The sample processing apparatus according to claim 1, further comprising a reading device configured to read, from the rack, the identification information of the rack.

12. The sample processing apparatus according to claim 1, wherein the rack has an area showing the identification information.

13. The sample processing apparatus according to claim 12, wherein the area is colored so that the rack having identification information corresponding to the special rack is able to be distinguished from either other types of racks or another type of rack.

14. The sample processing apparatus according to claim 1, wherein the plurality of sample processing units further includes a third sample processing unit, and
the at least one memory stores computer programs executed by the at least one processor to, if a third container is present in a third position of the rack, direct the at least one transport device to transport the rack to deliver the third container to the third sample processing unit.

15. The sample processing apparatus according to claim 1, wherein
the at least one memory stores computer programs executed by the at least one processor to, when the obtained identification information of the rack corresponds to a normal rack, assign the sample containers on the rack to one or more of the sample processing unit as destinations for each of the sample containers, so that each of the sample containers is assigned to the sample processing unit capable of measuring the sample in the sample container according to a measurement order requested for the sample.

16. The sample processing apparatus according to claim 15, wherein the normal rack carries one or more sample containers which accommodates a sample of a patient.

17. The sample processing apparatus according to claim 1, wherein the controller is configured to direct the at least one transport device to transport the rack to deliver the container to at least one of the sample processing units according to the measurement orders corresponding to the container, when the obtained identification information docs not correspond to the special rack.

18. A method for transporting a rack to or from one of a plurality of sample processing units through a transport path formed by at least one transport device, wherein the sample processing units includes at least first and second sample processing units and a rack comprises a plurality of positions configured to hold containers thereat, the method comprising computer executable steps performed by a processor of a computer system to implement:
obtaining identification information from a rack;
recognizing a presence or absence of a container with respect to each of the plurality of positions on the rack, when the obtained identification information of the rack corresponds to a special rack;
if a first container is present in a first position of the rack, determining the first sample processing unit to be a transport destination of the first container in accordance with recognizing the presence of the first container in the first position of the rack, and directing the at least one transport device to transport the rack to deliver the first container to the first sample processing unit; and
if a second container is present in a second position of the rack, determining the second sample processing unit to be a transport destination of the second container in accordance with recognizing the presence of the second container in the second position of the rack, and directing the at least one transport device to transport the rack to deliver the second container to the second sample processing unit.

19. The method according to claim 18, wherein the at least some of the positions in the rack are correlated to positions along the transport path of the at least some of the sample processing units.

20. The method according to claim 19, wherein the at least some of the positions in the rack are lined in an order correlated to an order in which the at least some of the sample processing units are positioned along the transport path.

21. The method according to claim 20, wherein the orders of the at least some of the positions in the rack and the positions of the at least some of the sample processing units are defined similarly by sequential numbers counted from upstream towards downstream of the transport path, and correlations between the at least some of the positions in the rack and the positions of the at least some of the sample processing units are established by same numbers of the orders.

22. The method according to claim 20, further comprising, after directing the at least one transport device to transport the rack to deliver the first container to the first sample processing unit, directing the at least one transport device to transport the rack from the first sample processing unit to deliver the second container held in the rack to the second sample processing unit.

23. The method according to claim 18, wherein the container on the rack may contain one of a sample for retesting, a cleaning liquid and a control sample.

* * * * *